(12) United States Patent
Kaula et al.

(10) Patent No.: US 12,420,102 B2
(45) Date of Patent: *Sep. 23, 2025

(54) SYSTEM, DEVICE, AND METHOD FOR GENERATING STIMULATION WAVEFORM HAVING A PARESTHESIA-INDUCING LOW-FREQUENCY COMPONENT AND A SPREAD-SPECTRUM HIGH-FREQUENCY COMPONENT

(71) Applicant: Cirtec Medical Corporation, Brooklyn Park, MN (US)

(72) Inventors: Norbert Kaula, Arvada, CO (US); Yohannes Iyassu, Denver, CO (US); Scott Brainard, Columbus Heights, MN (US)

(73) Assignee: Cirtec Medical Corporation, Brooklyn Park, MN (US)

( * ) Notice: Subject to any disclaimer, the term of this patent is extended or adjusted under 35 U.S.C. 154(b) by 492 days.

This patent is subject to a terminal disclaimer.

(21) Appl. No.: 17/491,756

(22) Filed: Oct. 1, 2021

(65) Prior Publication Data
US 2022/0016431 A1    Jan. 20, 2022

Related U.S. Application Data

(63) Continuation of application No. 15/976,618, filed on May 10, 2018, now Pat. No. 11,135,436.
(Continued)

(51) Int. Cl.
*A61N 1/00* (2006.01)
*A61N 1/36* (2006.01)
(Continued)

(52) U.S. Cl.
CPC ..... *A61N 1/37235* (2013.01); *A61N 1/36021* (2013.01); *A61N 1/36034* (2017.08);
(Continued)

(58) Field of Classification Search
CPC .................. A61N 1/37235; A61N 1/36125
(Continued)

(56) References Cited

U.S. PATENT DOCUMENTS

| 4,338,945 A | 7/1982 | Kosugi et al. |
| 6,188,929 B1 | 2/2001 | Giordano |

(Continued)

FOREIGN PATENT DOCUMENTS

| EP | 3103515 A1 * 12/2016 | ........... A61N 1/3605 |
| WO | WO 2015196164 | 12/2015 |

(Continued)

OTHER PUBLICATIONS

De Ridder, Dirk, et al., "Mimicking the Brain: Evaluation of St Jude Medical's Prodigy Chronic Pain System with Burst Technology", Expert Rev. Med. Devices, vol. 12, No. 2, pp. 143-150 (Dec. 2015).
(Continued)

*Primary Examiner* — Nicole F Johnson
(74) *Attorney, Agent, or Firm* — Haynes and Boone, LLP

(57) ABSTRACT

A pulse generator includes charging circuitry configured to provide electrical power to the pulse generator. The pulse generator includes communication circuitry configured to conduct wireless telecommunications with external programming devices. The telecommunications contain programming instructions sent from the external programming devices. The pulse generator includes stimulation circuitry configured to generate electrical pulses based on the programming instructions. The electrical pulses include a first component that is paresthesia-inducing and a second component that is non-paresthesia-inducing.

20 Claims, 18 Drawing Sheets

Related U.S. Application Data

(60) Provisional application No. 62/505,209, filed on May 12, 2017.

(51) Int. Cl.
*A61N 1/372* (2006.01)
*A61N 1/378* (2006.01)

(52) U.S. Cl.
CPC ..... *A61N 1/36071* (2013.01); *A61N 1/36125* (2013.01); *A61N 1/36132* (2013.01); *A61N 1/36146* (2013.01); *A61N 1/36171* (2013.01); *A61N 1/37217* (2013.01); *A61N 1/37247* (2013.01); *A61N 1/36153* (2013.01); *A61N 1/36157* (2013.01); *A61N 1/36175* (2013.01); *A61N 1/36185* (2013.01); *A61N 1/3787* (2013.01)

(58) Field of Classification Search
USPC .......................................................... 607/46
See application file for complete search history.

(56) References Cited

U.S. PATENT DOCUMENTS

| | | | |
|---|---|---|---|
| 6,501,307 | B1 | 12/2002 | Yen |
| 6,631,295 | B2 | 10/2003 | Rubinstein et al. |
| 7,047,078 | B2 | 5/2006 | Boggs, II et al. |
| 7,228,179 | B2 | 6/2007 | Campen et al. |
| 7,340,302 | B1 | 3/2008 | Falkenberg et al. |
| 7,483,747 | B2 | 1/2009 | Gliner et al. |
| 7,844,339 | B2 | 11/2010 | Buchner |
| 7,983,762 | B2 | 7/2011 | Gliner et al. |
| 8,301,263 | B2 | 10/2012 | Donofrio et al. |
| 8,359,102 | B2 | 1/2013 | Alataris et al. |
| 8,364,273 | B2 | 1/2013 | De Ridder |
| 8,644,941 | B2 | 2/2014 | Rooney et al. |
| 8,825,166 | B2 | 9/2014 | John |
| 8,843,209 | B2 | 9/2014 | Wacnik et al. |
| 8,914,119 | B2 | 12/2014 | Wu et al. |
| 9,387,325 | B1 | 7/2016 | Min et al. |
| 9,452,294 | B2 | 9/2016 | Kaula et al. |
| 9,492,667 | B1 | 11/2016 | Kent et al. |
| 9,533,152 | B2 | 1/2017 | Kilgard et al. |
| 9,550,063 | B2 | 1/2017 | Wolf |
| 2003/0135248 | A1* | 7/2003 | Stypulkowski .... A61N 1/36071 607/73 |
| 2005/0015117 | A1 | 1/2005 | Gerber |
| 2007/0027486 | A1 | 2/2007 | Armstrong |
| 2007/0100377 | A1 | 5/2007 | Armstrong et al. |
| 2007/0293917 | A1 | 12/2007 | Thompson et al. |
| 2009/0204173 | A1 | 8/2009 | Fang et al. |
| 2011/0009919 | A1 | 1/2011 | Carbunaru et al. |
| 2011/0184486 | A1 | 7/2011 | De Ridder |
| 2011/0184488 | A1* | 7/2011 | De Ridder ......... A61N 1/36153 607/46 |
| 2012/0095524 | A1 | 4/2012 | Nelson et al. |
| 2012/0203303 | A1 | 8/2012 | Alataris |
| 2014/0277281 | A1 | 9/2014 | Grandhe |
| 2015/0374986 | A1 | 12/2015 | Bahmer |
| 2016/0001087 | A1 | 1/2016 | Moffitt |
| 2016/0022992 | A1 | 1/2016 | Franke et al. |
| 2016/0074663 | A1* | 3/2016 | De Ridder ......... A61N 1/36196 607/59 |
| 2016/0158550 | A1 | 6/2016 | Hou et al. |
| 2016/0175589 | A1 | 6/2016 | Wingeier |
| 2016/0206877 | A1 | 7/2016 | Hargrove |
| 2016/0367812 | A1* | 12/2016 | De Ridder ......... A61N 1/36185 |
| 2018/0326220 | A1 | 11/2018 | Kaula et al. |

FOREIGN PATENT DOCUMENTS

| | | |
|---|---|---|
| WO | WO 2016086176 | 6/2016 |
| WO | WO 2018/035521 A1 | 2/2018 |

OTHER PUBLICATIONS

De Ridder, Dirk, et al., "A 2-Center Comparative Study on Tonic Versus Burst Spinal Cord Stimulation Amount of Responders and Amount of Pain Suppression", Clin. J. Pain, vol. 31, No. 5, pp. 433-437 (May 2015).

Joos, Kathleen, et al., "The Differential Effect of Low- Versus High-Frequency Random Noise Stimulation in the Treatment of Tinnitus", Exp. Brain Res., vol. 233, pp. 1433-1440 (Feb. 2015).

Freescale Semiconductor, Inc., "i.MX51 Applications Processors for Consumer and Industrial Products," Data Sheet Technical Data, Document No. IMX51CEC, Rev. 4 (Aug. 2010), 200 pages.

Texas Instruments, Inc., "Mixed Signal Microcontroller," brochure, MSP430G2x32, MSP430G2x02, SLAS723 (Dec. 2010), 53 pages.

European Patent Office, "European Search Report", Application No. 18172740.5, mailed Sep. 10, 2018, 9 pages.

\* cited by examiner

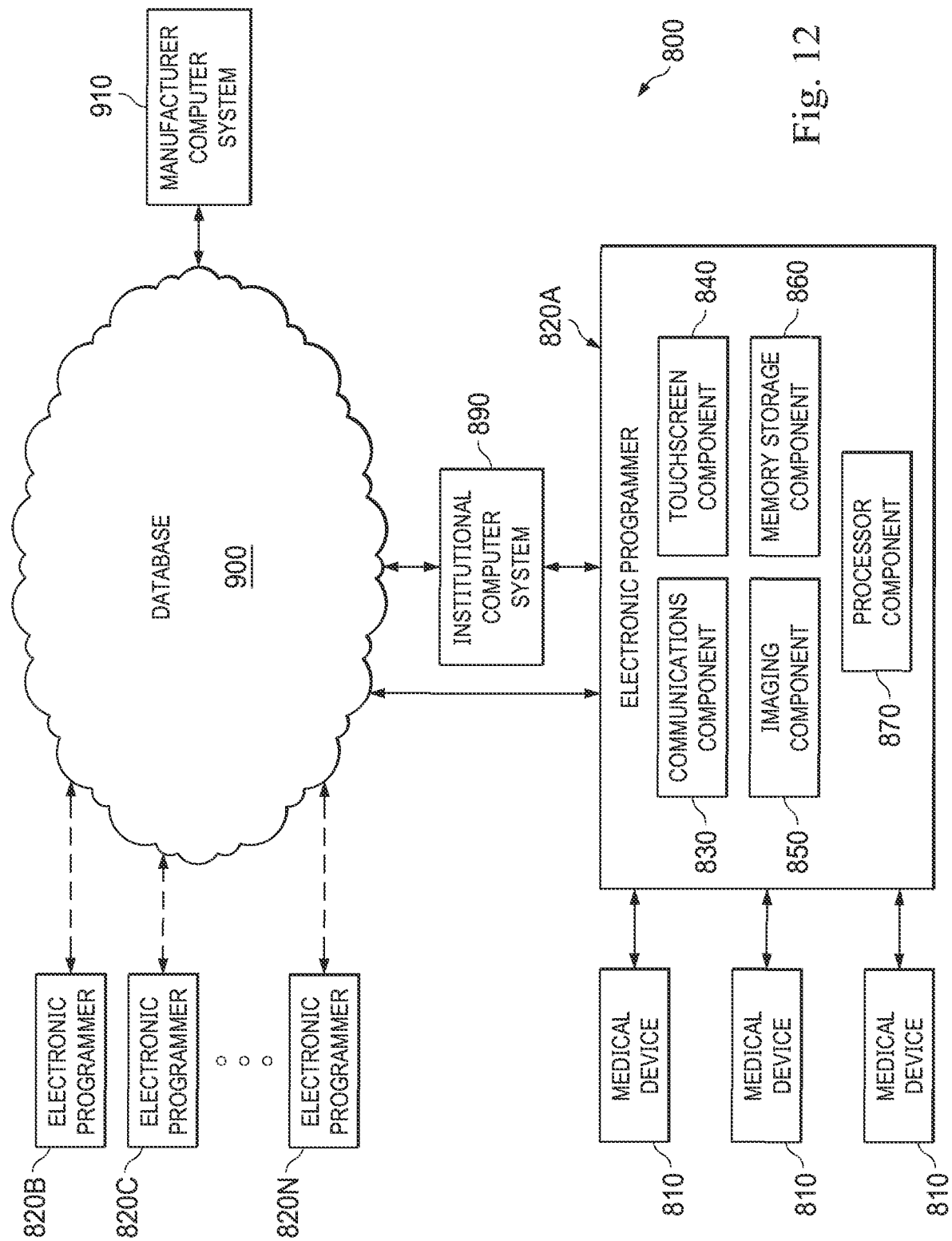

SYSTEM, DEVICE, AND METHOD FOR GENERATING STIMULATION WAVEFORM HAVING A PARESTHESIA-INDUCING LOW-FREQUENCY COMPONENT AND A SPREAD-SPECTRUM HIGH-FREQUENCY COMPONENT

CROSS REFERENCE TO RELATED APPLICATION

This application is a continuation of U.S. patent application Ser. No. 15/976,618, filed May 10, 2018, entitled "System, device, and method for generating stimulation waveform having a paresthesia-inducing low-frequency component and a spread-spectrum high-frequency component," now patented as U.S. Pat. No. 11,135,436, which claims benefit of U.S. Provisional Application No. 62/505,209, filed May 12, 2017, both of which are incorporated herein by reference in their respective entireties.

BACKGROUND

The invention relates to a stimulation system, such as spinal cord stimulation system, a peripheral nerve stimulation system, or a pelvic nerve or sacral nerve stimulation system. The stimulation system uses a pulse generator to provide electrical stimulation for a patient, for example to the spinal cord, a peripheral nerve, or a sacral nerve or a pudendal nerve, in order to treat problems such as chronic pain or incontinence. The pulse generator is coupled to a stimulation lead having one or more electrodes at a distal location thereof. The pulse generator provides the electrical stimulation through the electrodes via a body portion and connector of the lead. Stimulation programming in general refers to the configuring of stimulation electrodes and stimulation parameters to treat the patient using one or more implanted leads and its attached pulse generator. For example, the programming is typically achieved by selecting individual electrodes and adjusting the stimulation parameters, such as the shape of the stimulation waveform, amplitude of current in mA (or amplitude of voltage in V), pulse width in microseconds, frequency in Hz, and anodic or cathodic stimulation.

Despite recent advances in medical technology, existing stimulation methods, systems, and devices still have various shortcomings. For example, one problem faced by existing stimulation systems and methods is that they cannot provide a stimulation waveform that can optimize the stimulation therapy.

Therefore, although existing systems and methods for performing neurostimulation are generally adequate for their intended purposes, they have not been entirely satisfactory in all respects.

SUMMARY

One aspect of the present disclosure involves a pulse generator. The pulse generator includes charging circuitry configured to provide electrical power to the pulse generator. The pulse generator includes communication circuitry configured to conduct wireless telecommunications with external programming devices, the telecommunications containing programming instructions sent from the external programming devices. The pulse generator includes stimulation circuitry configured to generate electrical pulses based on the programming instructions. The electrical pulses include a first component that is paresthesia-inducing and a second component that is non-paresthesia-inducing. In some embodiments, the first component has a fixed frequency, and the second component has a spread-spectrum frequency range that is greater than the fixed frequency.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In the figures, elements having the same designation have the same or similar functions.

FIG. 12 is a simplified block diagram of a medical system/infrastructure according to various aspects of the present disclosure.

DETAILED DESCRIPTION

It is to be understood that the following disclosure provides many different embodiments, or examples, for implementing different features of the invention. Specific examples of components and arrangements are described below to simplify the present disclosure. These are, of course, merely examples and are not intended to be limiting. Various features may be arbitrarily drawn in different scales for simplicity and clarity.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
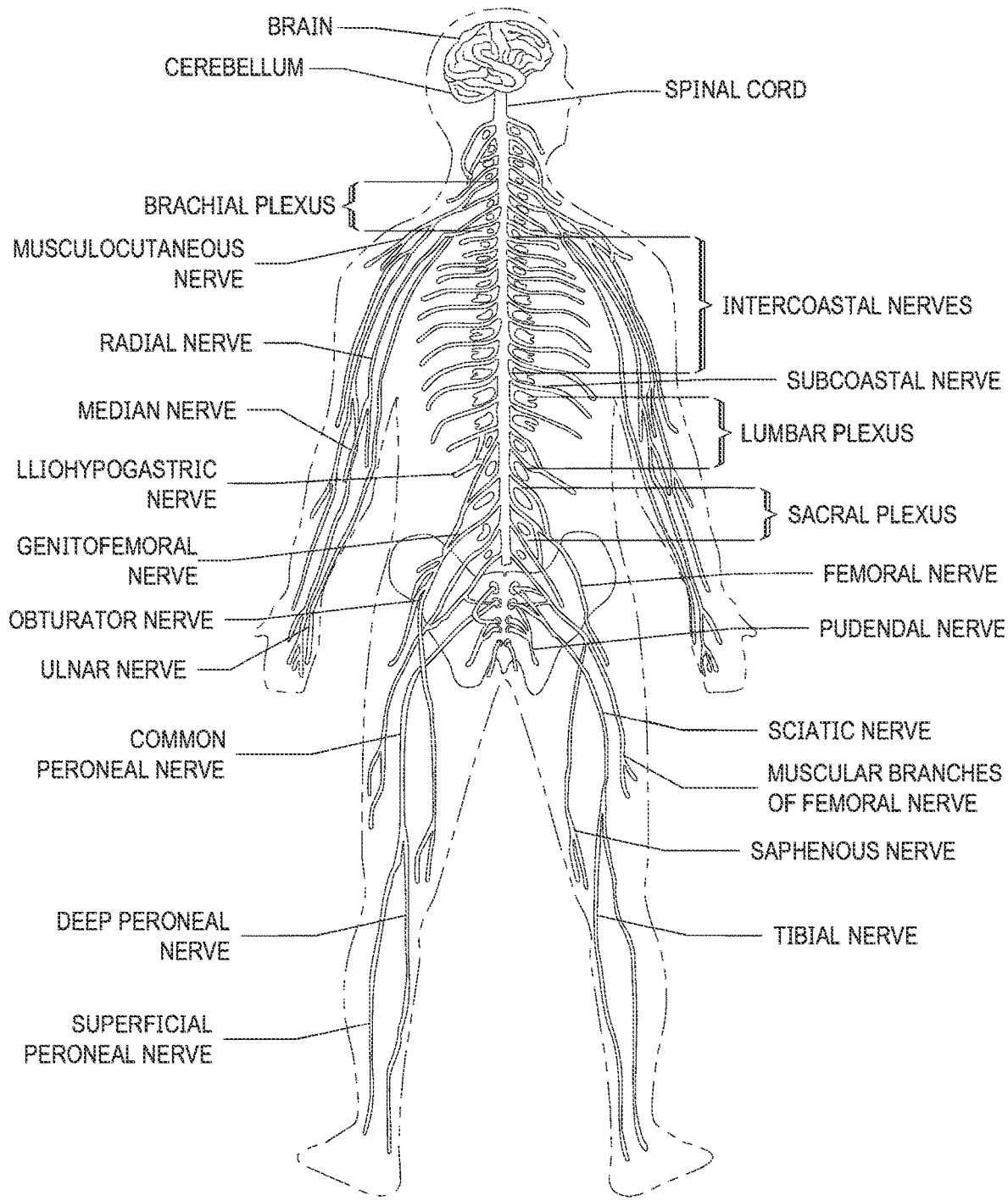
FIG. 1 is stylized overview of the human nervous system.

The human nervous system includes a complex network of neurological structures that extend throughout the body. As shown in FIG. 1, the brain interconnects with the spinal cord which branches into the brachial plexus near the shoulders and the lumbar plexus and sacral plexus in the lower back. The limb peripheral nerves of the arms extend distally from the brachial plexus down each arm. Similarly, the limb peripheral nerves of the legs extend distally from the lumbar plexus and sacral plexus. A number of the larger limb peripheral nerves are identified in FIG. 1. As discussed further below, certain aspects of the present invention are particularly well suited to stimulation of the pudendal nerves and the sacral nerves, including those identified in FIG. 1.

Figure 2B:
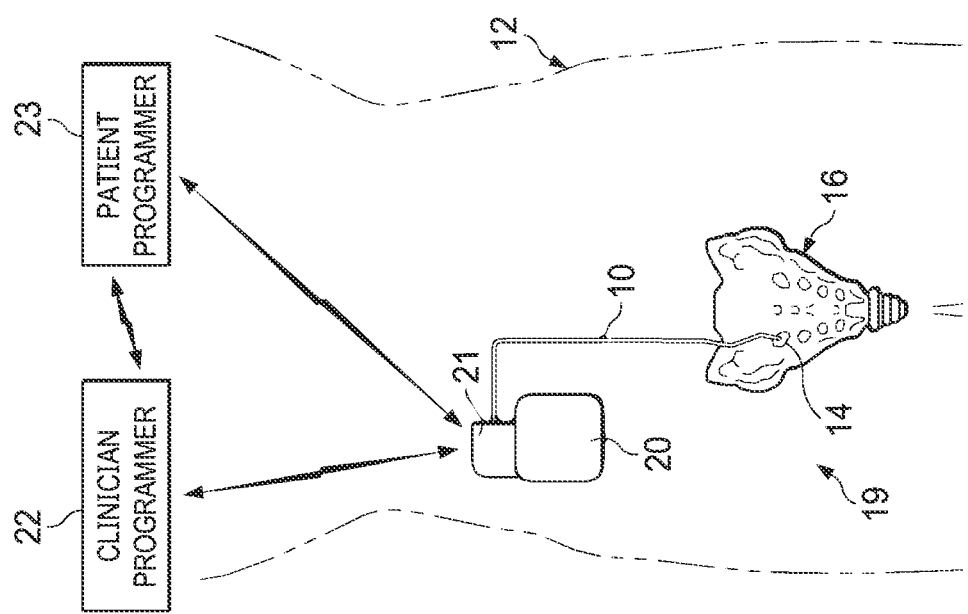
FIG. 2B is a simplified diagram illustrating an implantable neurostimulation system for stimulating nerves according to various embodiments of the present disclosure.
Figure 2A:
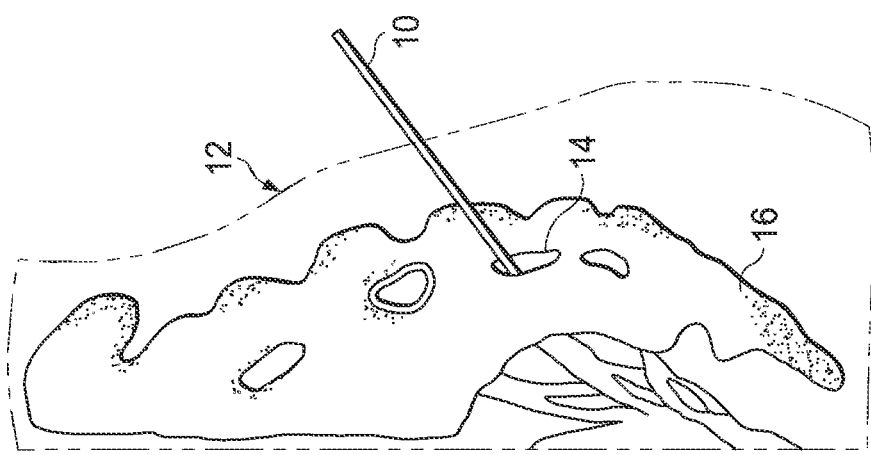
FIG. 2A is a diagram illustrating an example sacral implantation of a neurostimulation lead according to various embodiments of the present disclosure.
Figure 2D:
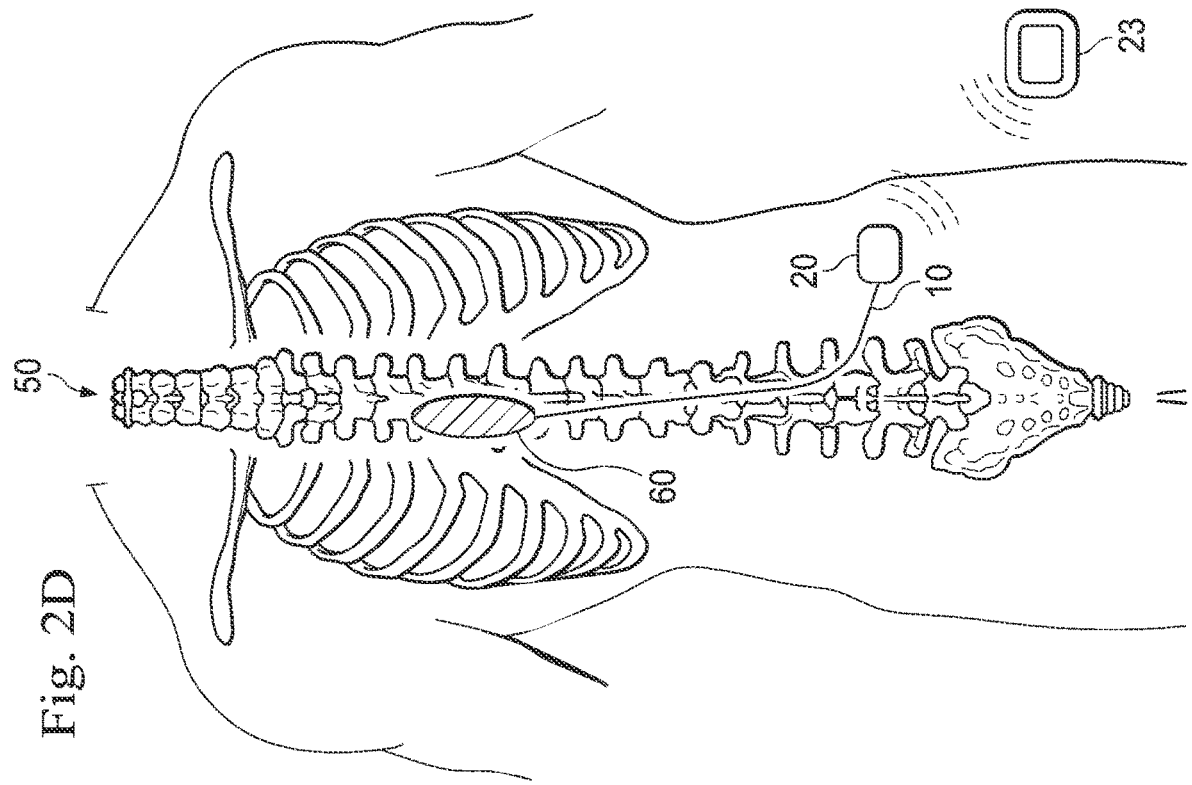
FIG. 2D is a simplified diagram illustrating a frontal view of a human spine for a context of spinal cord stimulation according to various embodiments of the present disclosure.
Figure 2C:
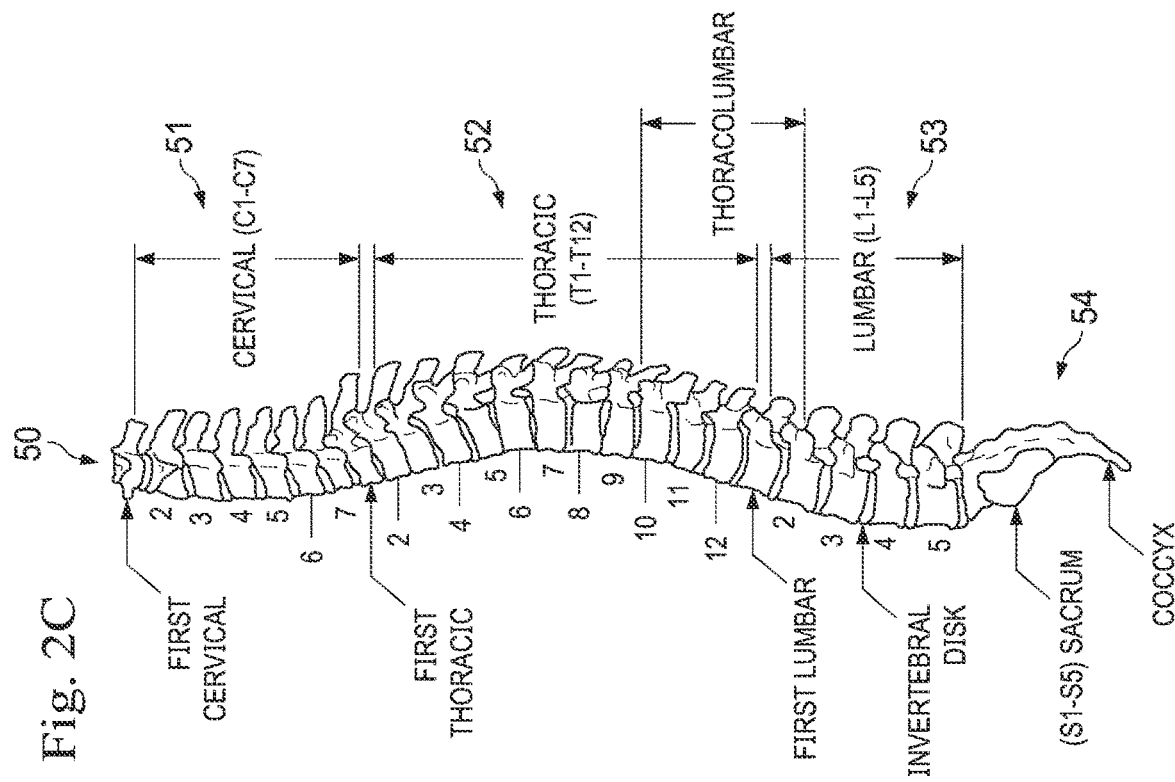
FIG. 2C is a simplified diagram illustrating a side view of a human spine according to various embodiments of the present disclosure.

FIG. 2A is a simplified diagram illustrating implantation of a neurostimulation lead 10. In the example of FIG. 2A, lead 10 is inserted into the body of a patient 12, and implanted posterior to one of dorsal foramen 14 of sacrum 16. However, lead 10 alternatively may be positioned to stimulate pudendal nerves, perineal nerves, sacral spinal nerves, or other areas of the nervous system. Lead 10 may be implanted via a needle and stylet for minimal invasiveness. Positioning of lead 10 may be aided by imaging techniques, such as fluoroscopy. In some embodiments, a plurality of stimulation leads may be provided.

FIG. 2B is a diagram illustrating an implantable neurostimulation system 19 for stimulating a nerve, such as a sacral nerve, via the lead 10. Neurostimulation system 19 delivers neurostimulation to the sacral nerves or other regions of the nervous system known to treat problems including, but are not limited to: pelvic floor disorders, urinary control disorders, fecal control disorders, interstitial cystitis, sexual dysfunction, and pelvic pain. As shown in FIG. 2B, system 19 includes lead 10 and an implantable pulse generator (IPG). In addition, a proximal end of stimulation lead 10 may be coupled to a connector block 21 associated with the neurostimulator 20.

In some embodiments, the neurostimulator 20 includes an implantable pulse generator (IPG), and delivers neurostimulation therapy to patient 12 in the form of electrical pulses generated by the IPG. In the example of FIG. 2B, the neurostimulator 20 is implanted in the upper left buttock of patient 12, but it is understood that the neurostimulator 20 be implanted at other locations in alternative embodiments.

The lead 10 carries one or more of stimulation electrodes, e.g., 1 to 8 electrodes, to permit delivery of electrical stimulation to the target nerve, such as the sacral nerve. For example, the implantable neurostimulation system 19 may stimulate organs involved in urinary, fecal or sexual function via C-fibers or sacral nerves at the second, third, and fourth sacral nerve positions, commonly referred to as S2, S3, and S4, respectively. In some embodiments, the neurostimulator 20 may be coupled to two or more leads deployed at different positions, e.g., relative to the spinal cord or sacral nerves.

The implantable neurostimulation system 19 also may include a clinician programmer 22 and a patient programmer 23. The clinician programmer 22 may be a handheld computing device that permits a clinician to program neurostimulation therapy for patient 12, e.g., using input keys and a display. For example, using clinician programmer 22, the clinician may specify neurostimulation parameters for use in delivery of neurostimulation therapy. The clinician programmer 22 supports radio frequency telemetry with neurostimulator 20 to download neurostimulation parameters and, optionally, upload operational or physiological data stored by the neurostimulator. In this manner, the clinician may periodically interrogate neurostimulator 20 to evaluate efficacy and, if necessary, modifies the stimulation parameters.

Similar to clinician programmer 22, patient programmer 23 may be a handheld computing device. The patient programmer 23 may also include a display and input keys to allow patient 12 to interact with patient programmer 23 and implantable neurostimulator 20. In this manner, the patient programmer 23 provides the patient 12 with an interface for control of neurostimulation therapy by neurostimulator 20. For example, the patient 12 may use patient programmer 23 to start, stop or adjust neurostimulation therapy. In particular, the patient programmer 23 may permit the patient 12 to adjust stimulation parameters such as duration, amplitude, pulse width and pulse rate, within an adjustment range specified by the clinician via the clinician programmer 22.

The neurostimulator 20, clinician programmer 22, and patient programmer 23 may communicate via wireless communication, as shown in FIG. 2B. The clinician programmer 22 and patient programmer 23 may, for example, communicate via wireless communication with neurostimulator 20 using RF telemetry techniques known in the art. The clinician programmer 22 and patient programmer 23 also may communicate with each other using any of a variety of local wireless communication techniques, such as RF communication according to the 802.11 or Bluetooth specification sets, or other standard or proprietary telemetry protocols. It is also understood that although FIG. 2B illustrates the patient programmer 23 and the clinician programmer 22 as two separate devices, they may be integrated into a single programmer in some embodiments.

The various aspects of the present disclosure will now be discussed in more detail below.

FIGS. 2A-2B illustrate the use of the IPG 20 in a spinal cord stimulation context according to some embodiments. In more detail, FIG. 2A is a side view of a spine 50, and FIG. 2B is a posterior view of the spine 50. The spine 50 includes a cervical region 51, a thoracic region 52, a lumbar region 53, and a sacrococcygeal region 54. The cervical region 51 includes the top 7 vertebrae, which may be designated with C1-C7. The thoracic region 52 includes the next 12 vertebrae below the cervical region 51, which may be designated with T1-T12. The lumbar region 53 includes the final 5 "true" vertebrae, which may be designated with L1-L5. The sacrococcygeal region 54 includes 9 fused vertebrae that make up the sacrum and the coccyx. The fused vertebrae of the sacrum may be designated with S1-S5.

Neural tissue (not illustrated for the sake of simplicity) branch off from the spinal cord through spaces between the vertebrae. The neural tissue can be individually and selectively stimulated in accordance with various aspects of the present disclosure. For example, referring to FIG. 2B, the IPG device 20 is implanted inside the body. The lead 10 is electrically coupled to the circuitry inside the IPG device 20. The conductive lead 10 may be removably coupled to the IPG device 20 through a connector, for example. A distal end of the conductive lead 10 is attached to one or more electrodes 60. The electrodes 60 are implanted adjacent to a desired nerve tissue in the thoracic region 52. Using well-established and known techniques in the art, the distal end of the lead 10 with its accompanying electrodes may be positioned along or near the epidural space of the spinal cord. It is understood that although only one conductive lead 10 is shown herein for the sake of simplicity, more than one conductive lead 10 and corresponding electrodes 60 may be implanted and connected to the IPG device 20.

The electrodes 60 deliver current drawn from the current sources in the IPG device 20, therefore generating an electric field near the neural tissue. The electric field stimulates the neural tissue to accomplish its intended functions. For example, the neural stimulation may alleviate pain in an embodiment. In other embodiments, a stimulator may be placed in different locations throughout the body and may be programmed to address a variety of problems, including for example but without limitation; prevention or reduction of epileptic seizures, weight control or regulation of heart beats.

It is understood that the IPG device 20, the lead 10, and the electrodes 60 may be implanted completely inside the body, may be positioned completely outside the body or may have only one or more components implanted within the body while other components remain outside the body. When they are implanted inside the body, the implant location may be adjusted (e.g., anywhere along the spine 50) to deliver the intended therapeutic effects of spinal cord electrical stimulation in a desired region of the spine. Furthermore, it is understood that the IPG device 20 may be controlled by a patient programmer or a clinician programmer 22, the implementation of which may be similar to the clinician programmer shown in FIG. 2B.

Figure 3A:
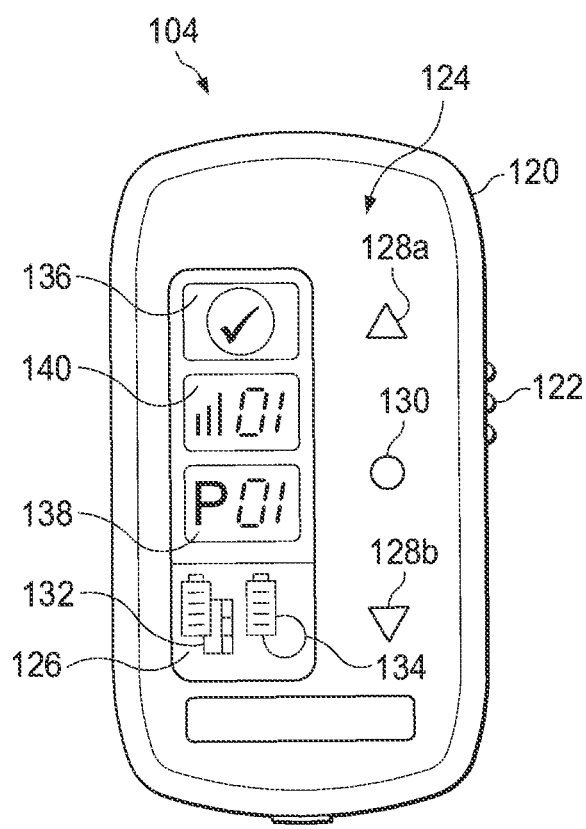
FIGS. 3A-3B illustrate an example pocket programmer controller in accordance with one embodiment of the present disclosure.
Figure 3B:
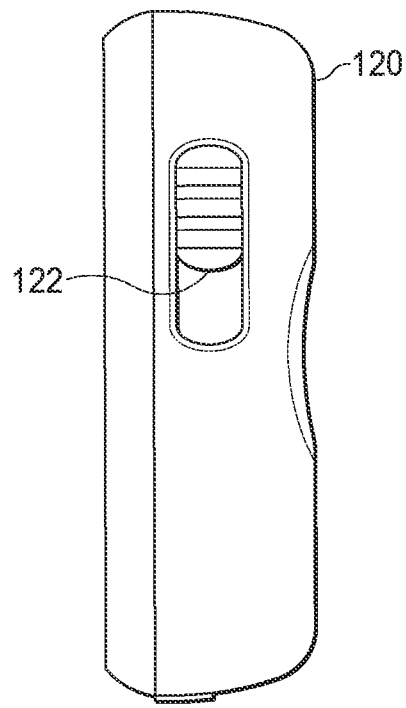
Figure 4:
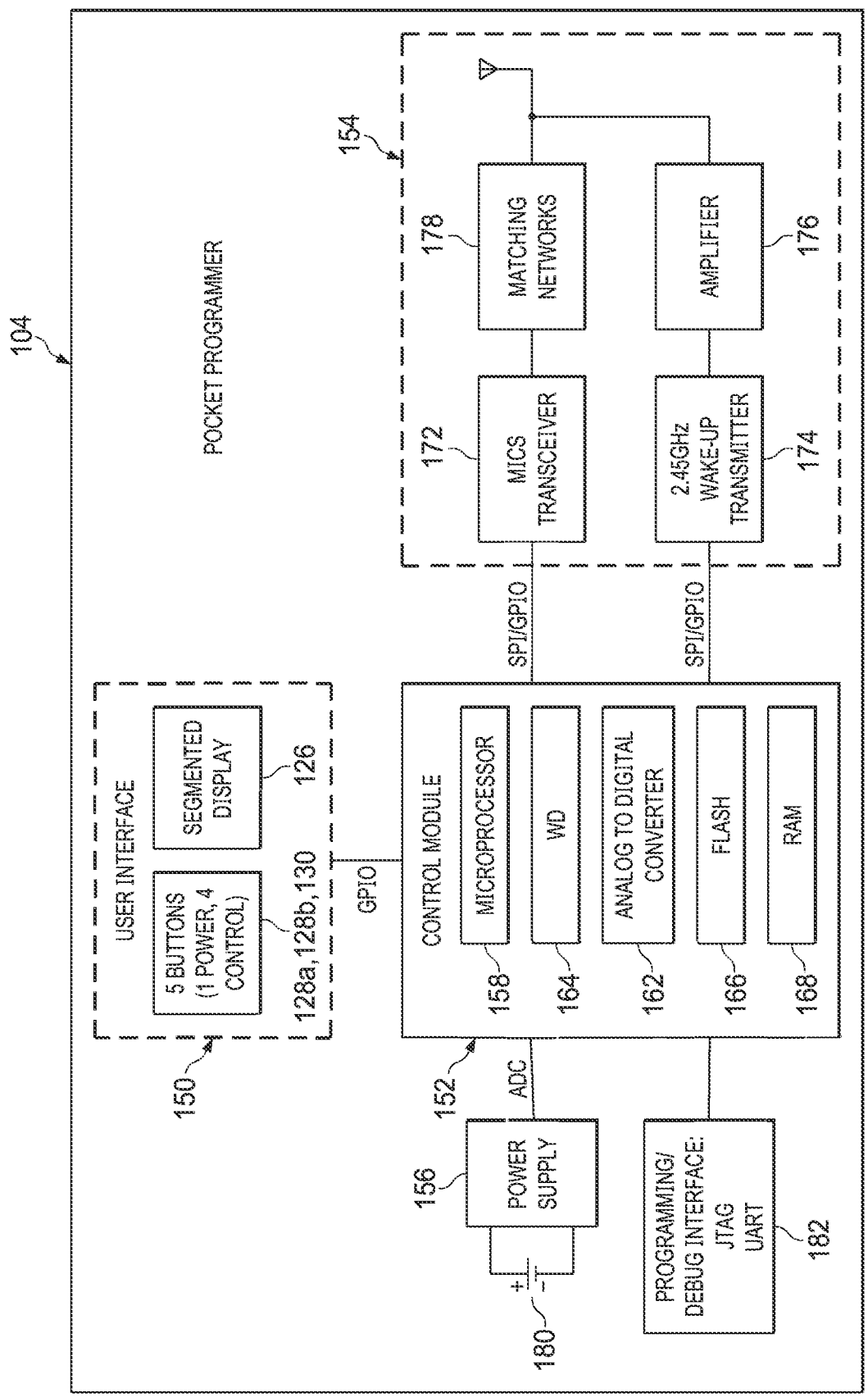
FIG. 4 is a block diagram of components of the example pocket controller of FIGS. 3A-3B in accordance with one embodiment of the present disclosure.
Figure 5A:
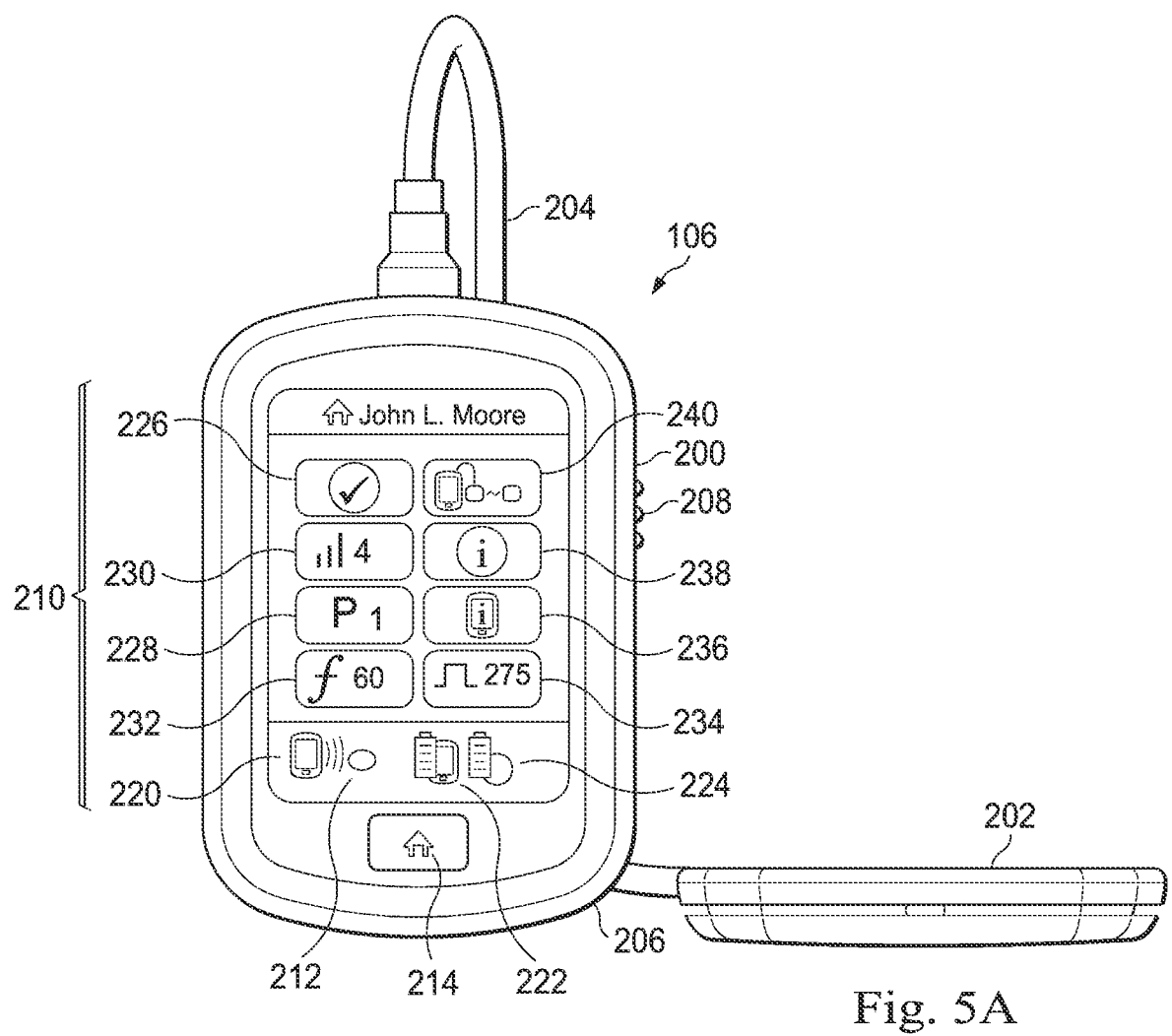
FIGS. 5A-5B illustrate an example patient programmer charger controller in accordance with one embodiment of the present disclosure.
Figure 5B:
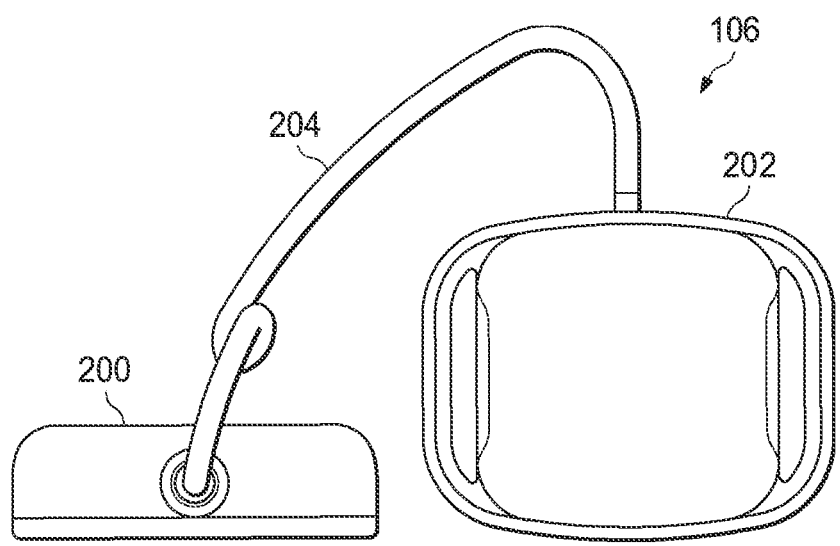
Figure 6:
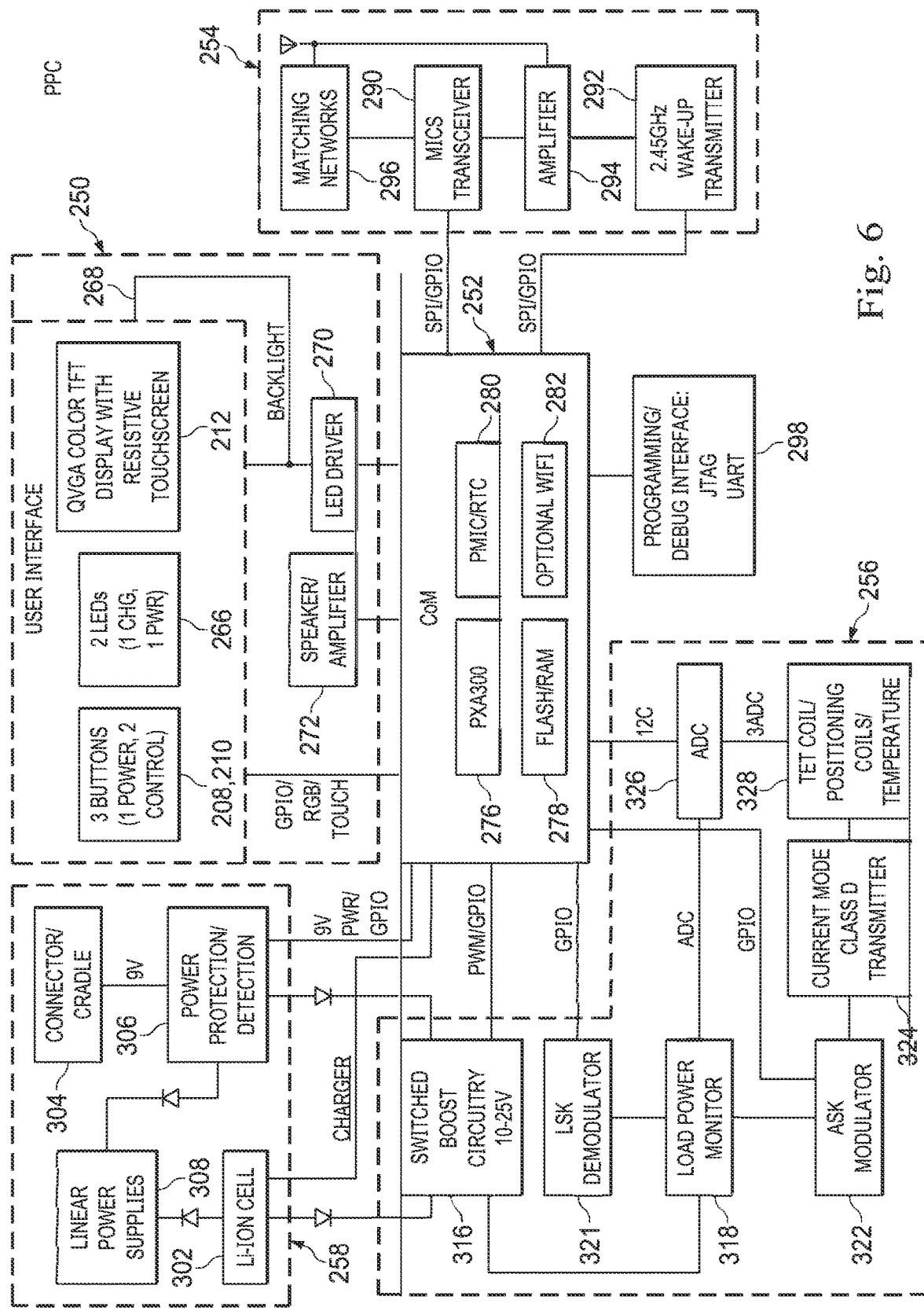
FIG. 6 is a block diagram of components of the example patient programmer charger of FIGS. 5A-5B in accordance with one embodiment of the present disclosure.

FIGS. 3A-3B, 4, 5A-5B, and 6 illustrate various example embodiments of the patient pocket programmer (hereinafter referred to as patient programmer for simplicity) according to various aspects of the present disclosure. In more detail, FIGS. 3A-3B, 4 are directed to a patient programmer that is implemented as a pocket controller 104, and FIGS. 5A-5B and 6 are directed to a patient programmer that is implemented as a patient programmer charger (PPC) 106.

Referring now to FIGS. 3A and 3B, the pocket controller 104 comprises an outer housing 120 having an on-off switch 122, a user interface comprising a plurality of control buttons 124, and a display 126. In this embodiment, the housing 120 is sized for discreetness and may be sized to fit easily in a pocket and may be about the same size as a key fob. In one example, the housing 120 forming the pocket controller 104 has a thickness of less than about 1.5 inch, a width of less than about 1.5 inch, and a height of less than about 3 inches. In another example, the housing 120 forming the pocket controller 104 has a thickness of about 0.8 inch, a width of about 1.4 inch, and a height of about 2.56 inch. However, both larger and smaller sizes are contemplated.

In this example, the control buttons 124 include two adjustment buttons 128a, 128b, a select button 130, and an emergency off button (not shown, but disposed on a side of the housing 120 opposing the on-off switch 122). The two adjustment buttons 128a, 128b allow a user to scroll or highlight available options and increase or decrease values shown on the display 126. The select button 130 allows a user to enter the value or select the highlighted options to be adjusted by actuation of the adjustment buttons 128a, 128b. In this example, the buttons 128a, 128b are used to navigate to one of the three available functions: 1) electrical stimulation on/off, 2) control stimulation amplitude adjustment, and 3) electrical stimulation program selection. Once the desired function is highlighted, the select button is pushed to allow changes (i.e. change the stimulation amplitude, select a different stimulation program, or turn the electrical stimulation on or off). In some examples, the IPG control functions of the pocket controller 104 consist of these functions. The emergency off button is disposed for easy access for a patient to turn off stimulation from the IPG 102 if the IPG provides too much stimulation or stimulation becomes uncomfortable for the patient. Allowing the user to scroll through the plurality of options (also referred to herein as operational parameters) that can be adjusted via the pocket controller 104 provides the user the confidence to carry only the pocket controller 104 while away from home. Users may be reluctant to carry only a conventional controller that allows adjustment of only a single operational parameter out of fear that they may need to adjust a different operational parameter while away from a more full-featured controller.

In the embodiment shown, the display 126 is an LCD display arranged to convey information to the user regarding selectable options, present settings, operating parameters and other information about the IPG 102 or the pocket controller 104. In this example, the display 126 shows the pocket controller's battery status at 132, the IPG's battery status at 134, the IPG's on or off status at 136, the currently selected electrical stimulation program at 138, and the amplitude setting of the running electrical stimulation program at 140. Other types of displays are also contemplated.

FIG. 4 shows a block diagram of components making up the pocket controller 104. It includes a user interface 150, a control module 152, a communication module 154, and a power storing controller 156. The user interface 150 is comprised of the buttons 128a, 128b, 130 and the display 126 described above with reference to FIG. 3A.

As can be seen, the user interface 150 is in communication with the control module 152. The control module 152 comprises a processor 158, memory, an analog-digital converter 162, and a watch dog circuit 164. The processor 158 may include a microprocessor, a controller, a digital signal processor (DSP), an application specific integrated circuit (ASIC), a field programmable gate array (FPGA), discrete logic circuitry, or the like. The processor 158 is configured to execute code or instructions provided in the memory. Here, the memory is comprised of flash memory 166 and RAM memory 168. However, the memory may include any volatile or non-volatile media, such as a random access memory (RAM), read only memory (ROM), non-volatile RAM (NVRAM), electrically erasable programmable ROM (EEPROM), flash memory, and the like. In some embodiments, the memory stores sets of stimulation control parameters that are available to be selected for delivery through the communication module 154 to the IPG 102 for electrical stimulation therapy. The AD converter 162 performs known functions of converting signals and the WD 164 is arranged to time out when necessary, such as in an event where the software becomes stuck in a loop. In one embodiment, the control module 152 comprises integrated circuits disposed on a PC board.

The communication module 154 comprises a medical implant communication service (MICS) RF transceiver 172 used to communicate with the IPG 102 to communicate desired changes and to receive status updates from and relating to the IPG 102, such as battery status and any error information. As used herein, MICS refers to wireless communications in a frequency band ranging from about 402 MHz to about 405 MHz, which is dedicated for communications with implanted medical devices. In this example, the MICS RF transceiver 172 utilizes a loop antenna for the communications with the IPG 102. Other antennas, such as, for example, dipole, chip antennas, or other known in the art also may be used. The communication module 154 also includes a wake up transmitter 174, an amplifier 176, and matching networks 178. The wake up transmitter 174 operates on a high frequency and is configured to send a short signal burst to wake up the IPG 102 when it is in a power-saving mode. Once the IPG 102 is ready, a communications link can be established between the IPG 102 and pocket controller 104, and communications can then occur over the MICS transceiver 172 using a standard frequency for a medical device transmission. The matching networks 178 tunes the antenna for optimum transmission power for the frequency selected. The pocket controller 104 also includes a programming interface 182. This may be used during manufacturing to load an operating system and program the pocket controller 104.

The power storing controller 156 is configured to convert power to recharge one or more rechargeable batteries 180. The batteries 180 provide power to operate the pocket controller 104 allowing it to receive user inputs and transmit control signals to the IPG 102. Some embodiments use primary cell batteries instead of rechargeable batteries. As indicated above, this pocket controller 104 is part of a larger system that contains the PPC 106 with a rich feature set for controlling the IPG 102 and includes an integrated battery charger used to charge the IPG's battery. By providing both the pocket controller 104 and the PPC 106, the patient can have a small unobtrusive device to carry around as they go about their daily business and a larger more full featured device which they can use in the comfort and privacy of their homes.

The pocket controller 104 is not only comfortable to carry in a pocket, but can also be attached to a key ring, lanyard, or other such carrying device for ease of daily use. Its functions are a subset of functions found on the PPC 106, and permit a user to power stimulation from the IPG on and off (i.e., the IPG 102 remains on, but stimulation is toggled between the on state when the IPG 102 is emitting electrical pulses and the off state when the IPG 102 is not emitting electrical pulses but remains in the standby mode for additional communications from the pocket controller 104, the PPC 106, or both), select which electrical stimulation program to run, and globally adjust the amplitude of electrical pulses emitted in a series of electrical pulses emitted by the IPG 102. By limiting the functions of the pocket controller to those most commonly used on a daily basis, the device becomes much less intimidating to the patient, and allows it to be kept very small. By keeping the device small, such as about key fob size, it becomes unobtrusive and the patient is more comfortable with having and using an implanted device.

FIGS. 5A-5B show the PPC 106 in greater detail. FIG. 5A is a front view of the PPC and FIG. 5B is a top view of FIG. 5A. The PPC 106 performs all the same operating functions as the pocket controller 104, but includes additional operating functions making it a multi-function full-featured, advanced patient controller charger. In the embodiment shown, the PPC 106 provides a simple but rich feature set to the more advanced user, along with the charging functions.

The PPC 106 includes a controller-charger portion 200 and a coil portion 202 connected by a flexible cable 204 and sharing components as described below. The controller-charger portion 200 comprises an outer housing 206 having an on-off switch 208 on its side, a plurality of control buttons 210, and a display 212, and an emergency off button (not shown, but disposed on a side of the housing 206 opposing the on-off switch 208). In this embodiment, the control buttons 210 are icons on the display 212, and the display is a full color, touch screen, graphical user interface. In addition, the controller-charger portion 200 includes a home button 214 configured to return the displayed images to a home screen. The controller-charger portion 200 is larger than the pocket controller 104 and in one embodiment is sized with a height greater than about 3 inches, a width greater than about 2.5 inches, and a thickness greater than about 0.8 inch. In another embodiment, the controller-charger portion is sized with a width of about 3.1 inches, a height of about 4.5 inches, and thickness of about 0.96 inches, although both larger and smaller sizes are contemplated.

In this example, the control buttons 210 allow a user to select a desired feature for control or further display. Particularly, the control buttons 210 enable functions of the PPC 106 that are the same as those of the pocket controller 104 (stimulation on/off, program stimulation amplitude adjustment, and stimulation program selection) along with additional features including: charging IPG battery, individual pulse stimulation amplitude adjustment that adjusts an amplitude of an individual pulse relative to the amplitude of an adjacent pulse in a series of pulses emitted by the IPG 102, stimulation program frequency adjustment, individual pulse width adjustment, detailed IPG status, detailed PPC status, PPC setup/configuration, a PPC battery status indicator, PPC to IPG communication status indicator, and other items and functions. The detailed IPG status may include, for example, IPG serial number and IPG software revision level. Detailed PPC status may include, for example, date and time setting, brightness control, audio volume and mute control, and PPC serial number and software revision level.

By having a pocket controller 104 that is limited to a plurality, such as only three controls (stimulation on/off, program amplitude adjust, and stimulation program selection), for example, a user can quickly and easily identify and select the features that are most commonly used. Features that are used less frequently, such as IPG recharge, are included on the full-featured PPC, but not the pocket controller 104. Features that are seldom accessed, or not accessed at all by some users, including individual pulse amplitude adjust, pulse width adjust, stimulation program frequency adjust, or serial number and software revision information, are also not included on the limited-feature pocket controller, but are included on the PPC. This allows the pocket controller to be significantly smaller, with a very simple and easy to user interface, as compared to systems that need to support all of these features.

Referring to the example shown in FIG. 5A, the touch screen display 212 is arranged to convey information to the user regarding selectable options, current settings, operating parameters and other information about the IPG 102 or the PPC 106. In this example, the display 212 shows a MICS communication indicator 220, the PPC's battery status at 222, the IPG's battery status at 224, the IPG's on or off status at 226, the currently selected electrical stimulation program at 228, and the amplitude setting of the active electrical stimulation program at 230. In addition, the display 212 shows the frequency 232, the pulse width setting 234, a selectable status icon for accessing detailed PPC information 236, a selectable status icon for accessing detailed IPG information 238, and a selectable icon for enabling IPG charging 240. Selecting any single icon may activate another menu within that selected subject area. The controller-charger portion 200 may include a rechargeable battery whose charge status is shown by the PPC's battery status at 222.

The coil portion 202 is configured to wirelessly charge the batteries in the IPG 102. In use, the coil portion 202 is applied against the patient's skin or clothing externally so that energy can be inductively transmitted and stored in the IPG battery. As noted above, the coil portion 202 is connected with the integrated controller-charger portion 200. Accordingly, the controller-charger portion 200 can simultaneously display the current status of the coil portion 204, the battery power level of the IPG 102, as well as the battery power level of the PPC. Accordingly, controlling and charging can occur in a more simplistic, time-effective manner, where the patient can perform all IPG maintenance in a single sitting. In addition, since the most commonly used features of the PPC 106 are already functional on the pocket controller, the PPC 106 may be left at home when the user does not desire to carry the larger, more bulky PPC.

FIG. 6 shows a block diagram of the components making up the PPC 106. It includes a user interface 250, a control module 252, a communication module 254, an IPG power charging module 256, and a power storing module 258. The user interface 250 is comprised of the buttons 210 and the display 212 described above. In this embodiment however, the user interface 250 also includes one or more LEDs 266 signifying whether the PPC 106 is charging or powered on and a backlight 268 that illuminates the color display. In some embodiments, these LEDs may have colors symbolizing the occurring function. An LED driver 270 and a speaker or amplifier 272 also form a part of the user interface 250.

As can be seen, the user interface 250 is in communication with the control module 252. The control module 252 comprises a processor 276, memory 278, and a power management integrated circuit (PMIC)/real time clock (RTC) 280. In the example shown, the control module 252 also includes a Wi-Fi RF transceiver 282 that allows the PPC 106 to connect to a wireless network for data transfer. For example, it may permit doctor-patient interaction via the internet, remote access to PPC log files, remote diagnostics, and other information transfer functions. The PMIC 280 is configured to control the charging aspects of the PPC 106. The Wi-Fi transceiver 282 enables Wi-Fi data transfer for programming the PPC 106, and may permit wireless access to stored data and operating parameters. Some embodiments also include a Bluetooth RF transceiver for communication with, for example, a Bluetooth enabled printer, a keyboard, etc.

In one embodiment, the control module 252 also includes an AD converter and a watch dog circuit as described above with reference to the control module 252. Here, the memory 278 is comprised of flash memory and RAM memory, but may be other memory as described above. In some embodiments, the processor 276 is an embedded processor running a WinCE operating system (or any real time OS) with the graphics interface 250, and the memory 278 stores sets of stimulation control parameters that are available to be selected for delivery through the communication module 254 to the IPG 102 for electrical stimulation therapy. In one embodiment, the control module 252 comprises integrated circuits disposed on a PC board.

The communication module 254 comprises a MICS RF transceiver 290, a wake up transmitter 292, an amplifier 294, and matching networks 296. The communication module 254 may be similar to the communication module 154 discussed above, and will not be further described here. The PPC 106 also includes a programming interface 298 that may be used during manufacturing to load an operating system and program the PPC 106.

The power storing module 258 is configured to convert power to recharge one or more rechargeable batteries 302. In this embodiment, the batteries 302 are lithium-ion cells that provide power to operate the PPC 106 allowing it to receive user inputs, transmit control signals to, and charge the IPG 102. The power storing module 258 includes a connector 304 for connecting to a power source, a power protection detection circuit 306 for protecting the PPC from power surges, and linear power supplies 308 for assisting with the electric transfer to charge the batteries 302. As can be seen, the control module 252 aids with the charging and is configured to monitor and send the battery charge level to the user interface 250 for display. The connector 304 connects the PPC, directly or indirectly, to a power source (not shown) such as a conventional wall outlet for receiving electrical current. In some embodiments, the connector 304 comprises a cradle.

The power charging module 256 communicates with the control module 252 and is arranged to magnetically or inductively charge the IPG 102. In the embodiments shown, it is magnetically or inductively coupled to the IPG 102 to charge rechargeable batteries on the IPG 102. The charging module 256 includes components in both the controller-charger portion 200 and the coil portion 202 (FIGS. 5A-5B). It includes switch boost circuitry 316, a load power monitor 318, an LSK demodulator 321, a ASK modulator 322, a current mode transmitter 324, an ADC 326, and coils 328. As can be seen, the control module 252 aids with the charging and is configured to monitor and send the IPG battery charge level to the user interface 250 for display.

In this embodiment, the coils 328 are disposed in the coil portion 202 and are configured to create magnetic or inductive coupling with components in the IPG 102. Since the coil portion 202 is integrated with the controller-charger portion 200, both operate from a single battery 302. Accordingly, as can be seen by the circuitry, the battery 302 powers the control module 252 and all its associated components. In addition, the battery 302 powers the power charging module 256 for recharging the IPG 102.

Because the coil portion 202 is integrated with the controller-charger portion 200, the control module 252 provides a single control interface and a single user interface for performing both functions of controlling the IPG 102 and of charging the IPG 102. In addition, because the controller-charger portion 200 and the coil portion 202 are integrated, the controller-charger portion 200 simultaneously controls both the current status of the charger, the battery power level of the IPG 102, as well as the battery power level of the PPC. Accordingly, controlling and charging can occur in a more simplistic, time-effective manner, where the patient can perform all IPG maintenance in a single sitting. In addition, since the most commonly used features of the PPC 106 are already functional on the pocket controller, the PPC 106 may be left at home when the user does not desire to carry the larger, more bulky PPC.

Figure 7:
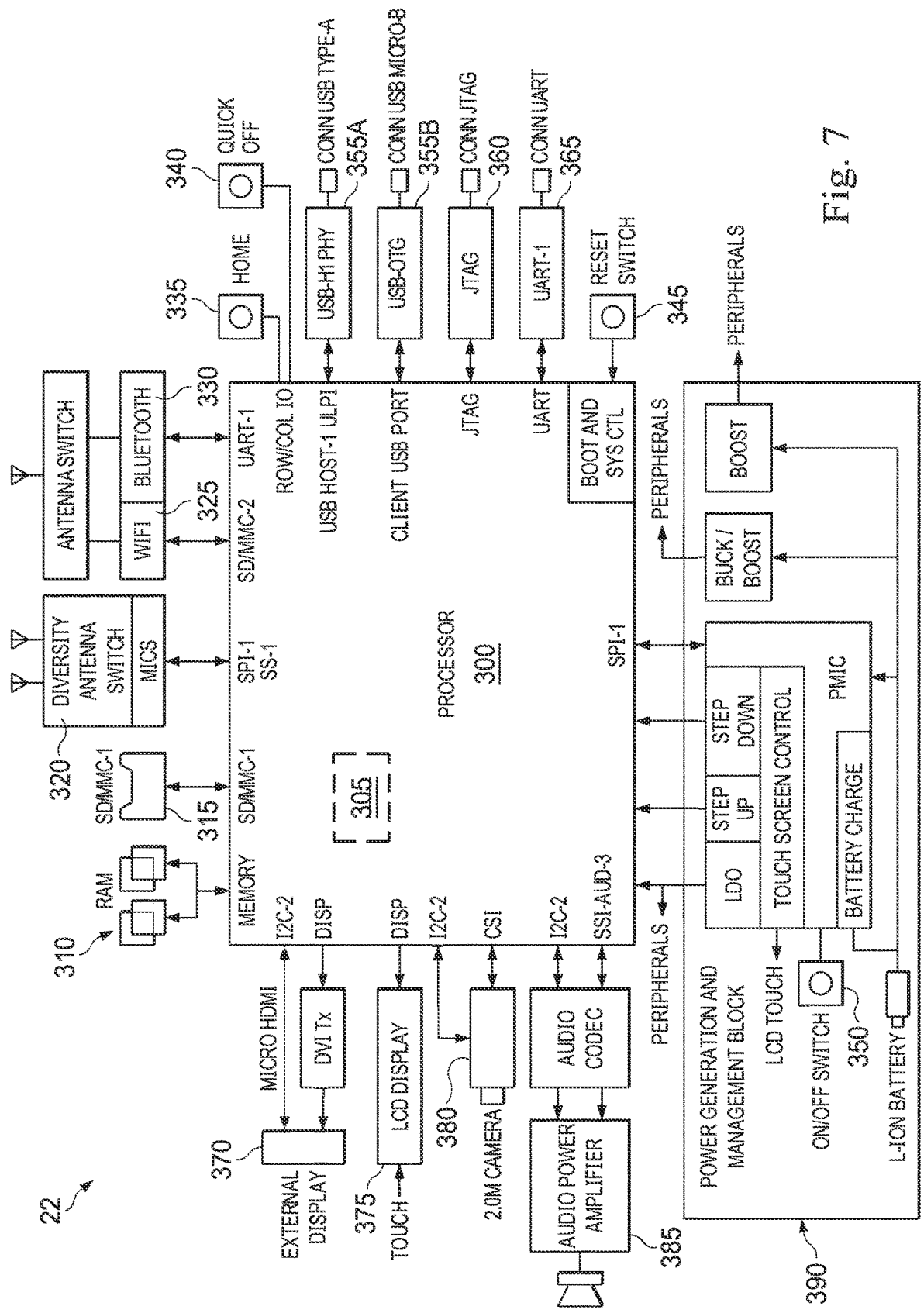
FIG. 7 is a block diagram of a clinician programmer according to one embodiment of the present disclosure.

FIG. 7 shows a block diagram of one example embodiment of a clinician programmer (CP), for example the CP 22 shown in FIG. 2B. The CP 22 includes a printed circuit board ("PCB") that is populated with a plurality of electrical and electronic components that provide power, operational control, and protection to the CP 22. With reference to FIG. 7, the CP includes a processor 300. The processor 300 is a controller for controlling the CP 22 and, indirectly, the IPG 20 as discussed further below. In one construction, the processor 300 is an applications processor model i.MX515 available from Freescale Semiconductor. More specifically, the i.MX515 applications processor has internal instruction and data cashes, multimedia capabilities, external memory interfacing, and interfacing flexibility. Further information regarding the i.MX515 applications processor can be found in, for example, the "IMX510EC, Rev. 4" data sheet; dated August 2010; published by Freescale Semiconductor at www.freescale.com, the content of the data sheet being incorporated herein by reference. Of course, other processing units, such as other microprocessors, microcontrollers, digital signal processors, etc., can be used in place of the processor 300.

The CP 22 includes memory, which can be internal to the processor 300 (e.g., memory 305), external to the processor 300 (e.g., memory 310), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The processor 300 executes software that is capable of being stored in the RAM (e.g., during execution), the ROM (e.g., on a generally permanent basis), or another non-transitory computer readable medium such as another memory or a disc. The CP 22 also includes input/output ("I/O") systems that include routines for transferring information between components within the processor 300 and other components of the CP 22 or external to the CP 22.

Software included in the implementation of the CP 22 is stored in the memory 305 of the processor 300, memory 310 (e.g., RAM or ROM), or external to the CP 22. The software includes, for example, firmware, one or more applications, program data, one or more program modules, and other executable instructions. The processor 300 is configured to retrieve from memory and execute, among other things, instructions related to the control processes and methods described below for the CP 22. For example, the processor 300 is configured to execute instructions retrieved from the memory 140 for establishing a protocol to control the IPG 20.

One memory shown in FIG. 7 is memory 310, which can be a double data rate (DDR2) synchronous dynamic random access memory (SDRAM) for storing data relating to and captured during the operation of the CP 22. In addition, a secure digital (SD) multimedia card (MMC) can be coupled to the CP for transferring data from the CP to the memory card via slot 315. Of course, other types of data storage devices can be used in place of the data storage devices shown in FIG. 7.

The CP 22 includes multiple bi-directional radio communication capabilities. Specific wireless portions included with the CP 22 are a Medical Implant Communication Service (MICS) bi-direction radio communication portion 320, a Wi-Fi bi-direction radio communication portion 325, and a Bluetooth bi-direction radio communication portion 330. The MICS portion 320 includes a MICS communication interface, an antenna switch, and a related antenna, all of which allows wireless communication using the MICS specification. The Wi-Fi portion 325 and Bluetooth portion 330 include a Wi-Fi communication interface, a Bluetooth communication interface, an antenna switch, and a related antenna all of which allows wireless communication following the Wi-Fi Alliance standard and Bluetooth Special Interest Group standard. Of course, other wireless local area network (WLAN) standards and wireless personal area networks (WPAN) standards can be used with the CP 22.

The CP 22 includes three hard buttons: a "home" button 335 for returning the CP to a home screen for the device, a "quick off" button 340 for quickly deactivating stimulation IPG, and a "reset" button 345 for rebooting the CP 22. The CP 22 also includes an "ON/OFF" switch 350, which is part of the power generation and management block (discussed below).

The CP 22 includes multiple communication portions for wired communication. Exemplary circuitry and ports for receiving a wired connector include a portion and related port for supporting universal serial bus (USB) connectivity 355, including a Type-A port and a Micro-B port; a portion and related port for supporting Joint Test Action Group (JTAG) connectivity 360, and a portion and related port for supporting universal asynchronous receiver/transmitter (UART) connectivity 365. Of course, other wired communication standards and connectivity can be used with or in place of the types shown in FIG. 7.

Another device connectable to the CP 22, and therefore supported by the CP 22, is an external display. The connection to the external display can be made via a micro High-Definition Multimedia Interface (HDMI) 370, which provides a compact audio/video interface for transmitting uncompressed digital data to the external display. The use of the HDMI connection 370 allows the CP 22 to transmit video (and audio) communication to an external display. This may be beneficial in situations where others (e.g., the surgeon) may want to view the information being viewed by the healthcare professional. The surgeon typically has no visual access to the CP 22 in the operating room unless an external screen is provided. The HDMI connection 370 allows the surgeon to view information from the CP 22, thereby allowing greater communication between the clinician and the surgeon. For a specific example, the HDMI connection 370 can broadcast a high definition television signal that allows the surgeon to view the same information that is shown on the LCD (discussed below) of the CP 22.

The CP 22 includes a touch screen I/O device 375 for providing a user interface with the clinician. The touch screen display 375 can be a liquid crystal display (LCD) having a resistive, capacitive, or similar touch-screen technology. It is envisioned that multitouch capabilities can be used with the touch screen display 375 depending on the type of technology used.

The CP 22 includes a camera 380 allowing the device to take pictures or video. The resulting image files can be used to document a procedure or an aspect of the procedure. For example, the camera 380 can be used to take pictures of barcodes associated with the IPG 20 or the leads, or documenting an aspect of the procedure, such as the positioning of the leads. Similarly, it is envisioned that the CP 22 can communicate with a fluoroscope or similar device to provide further documentation of the procedure. Other devices can be coupled to the CP 22 to provide further information, such as scanners or RFID detection. Similarly, the CP 22 includes an audio portion 385 having an audio codec circuit, audio power amplifier, and related speaker for providing audio communication to the user, such as the clinician or the surgeon.

The CP 22 further includes a power generation and management block 390. The power generation and management block 390 has a power source (e.g., a lithium-ion battery) and a power supply for providing multiple power voltages to the processor, LCD touch screen, and peripherals.

Figure 8:
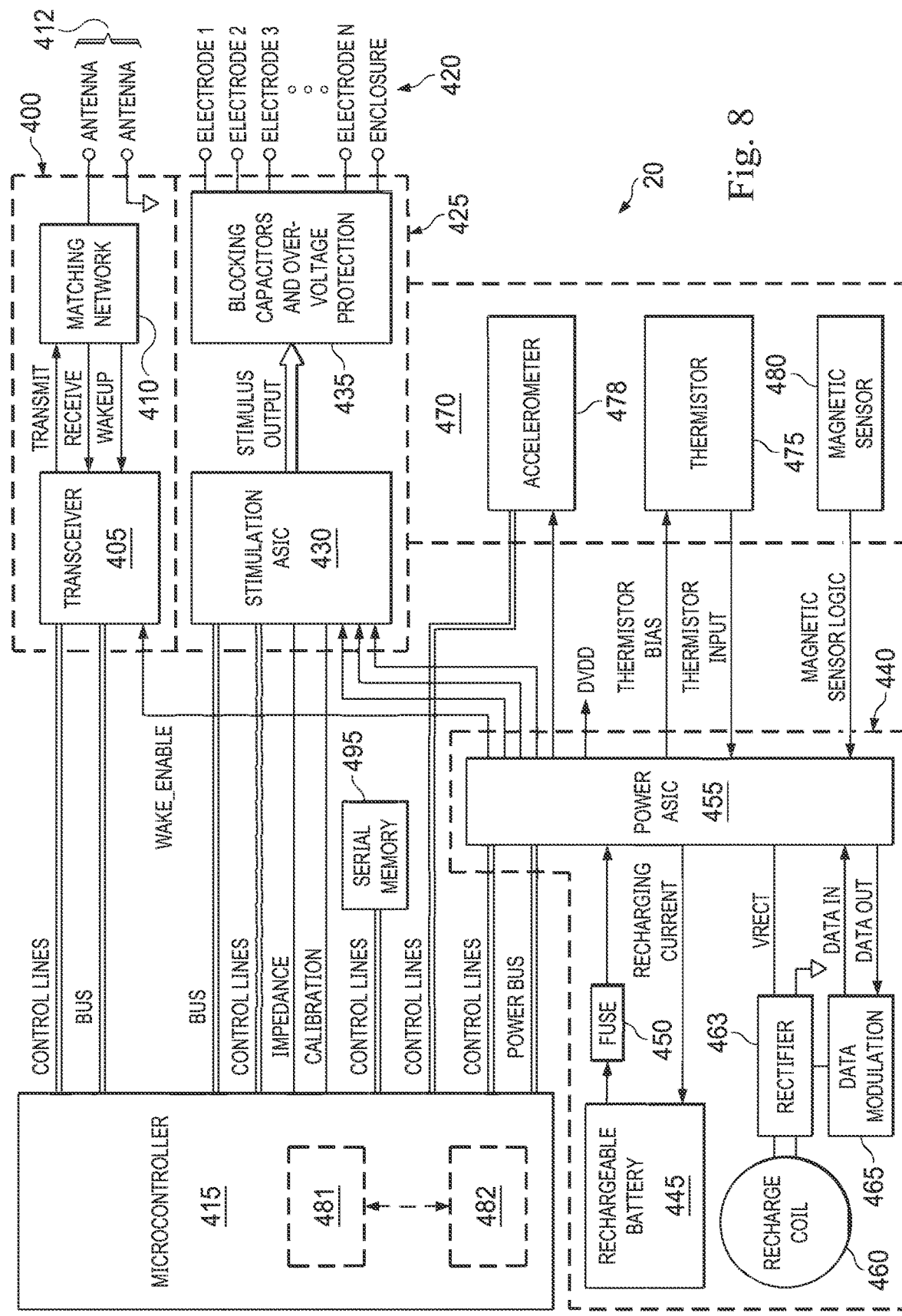
FIG. 8 is a block diagram of an implantable pulse generator according to one embodiment of the present disclosure.

FIG. 8 shows a block diagram of an example embodiment of an IPG, for example an embodiment of the IPG 20 shown in FIG. 2B. The IPG 20 includes a printed circuit board ("PCB") that is populated with a plurality of electrical and electronic components that provide power, operational control, and protection to the IPG 20. With reference to FIG. 8, the IPG 20 includes a communication portion 400 having a transceiver 405, a matching network 410, and antenna 412. The communication portion 400 receives power from a power ASIC (discussed below), and communicates information to/from the microcontroller 415 and a device (e.g., the CP 22) external to the IPG 20. For example, the IPG 20 can provide bi-direction radio communication capabilities, including Medical Implant Communication Service (MICS) bi-direction radio communication following the MICS specification.

The IPG 20, as previously discussed, provides stimuli to electrodes of an implanted medical electrical lead 110. As shown in FIG. 8, 1-N electrodes are connected to the IPG 20. In addition, the enclosure or housing 420 of the IPG 20 can act as an electrode. The stimuli are provided by a stimulation portion 425 in response to commands from the microcontroller 415. The stimulation portion 425 includes a stimulation application specific integrated circuit (ASIC) 430 and circuitry including blocking capacitors and an over-voltage protection circuit. As is well known, an ASIC is an integrated circuit customized for a particular use, rather than for general purpose use. ASICs often include processors, memory blocks including ROM, RAM, EEPROM, Flash, etc. The stimulation ASIC 430 can include a processor, memory, and firmware for storing preset pulses and protocols that can be selected via the microcontroller 415. The providing of the pulses to the electrodes is controlled through the use of a waveform generator and amplitude multiplier of the stimulation ASIC 430, and the blocking capacitors and overvoltage protection circuitry of the stimulation portion 425, as is known in the art. The stimulation portion 425 of the IPG 20 receives power from the power ASIC (discussed below). The stimulation ASIC 430 also provides signals to the microcontroller 415. More specifically, the stimulation ASIC 430 can provide impedance values for the channels associated with the electrodes, and also communicate calibration information with the microcontroller 415 during calibration of the IPG 20.

The IPG 20 also includes a power supply portion 440. The power supply portion includes a rechargeable battery 445, fuse 450, power ASIC 455, recharge coil 460, rectifier 463 and data modulation circuit 465. The rechargeable battery 445 provides a power source for the power supply portion 440. The recharge coil 460 receives a wireless signal from the PPC 135. The wireless signal includes an energy that is converted and conditioned to a power signal by the rectifier 463. The power signal is provided to the rechargeable battery 445 via the power ASIC 455. The power ASIC 455 manages the power for the IPG 20. The power ASIC 455 provides one or more voltages to the other electrical and electronic circuits of the IPG 155. The data modulation circuit 465 controls the charging process.

The IPG also includes a sensor section 470 that includes a thermistor 475, an accelerometer 478, and a magnetic sensor 480. The thermistor 475 detects temperature of the IPG. The accelerometer 478 detects motion or movement of the IPG, and the magnetic sensor 480 provides a "hard" switch upon sensing a magnet for a defined period. The signal from the magnetic sensor 480 can provide an override for the IPG 20 if a fault is occurring with the IPG 20 and is not responding to other controllers. The magnetic sensor 480 can also be used to turn on and off stimulation.

The IPG 20 is shown in FIG. 8 as having a microcontroller 415. Generally speaking, the microcontroller 415 is a controller for controlling the IPG 20. The microcontroller 415 includes a suitable programmable portion 481 (e.g., a microprocessor or a digital signal processor), a memory 482, and a bus or other communication lines. An exemplary microcontroller capable of being used with the IPG is a model MSP430 ultra-low power, mixed signal processor by Texas Instruments. More specifically, the MSP430 mixed signal processor has internal RAM and flash memories, an internal clock, and peripheral interface capabilities. Further information regarding the MSP 430 mixed signal processor can be found in, for example, the "MSP430G2x32, MSP430G2x02 MIXED SIGNAL MICROCONTROLLER" data sheet; dated December 2010, published by Texas Instruments at www.ti.com; the content of the data sheet being incorporated herein by reference.

The IPG 20 includes memory, which can be internal to the control device (such as memory 482), external to the control device (such as serial memory 495), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The programmable portion 481 executes software that is capable of being stored in the RAM (e.g., during execution), the ROM (e.g., on a generally permanent basis), or another non-transitory computer readable medium such as another memory or a disc.

Software included in the implementation of the IPG 20 is stored in the memory 482. The software includes, for example, firmware, one or more applications, program data, one or more program modules, and other executable instructions. The programmable portion 481 is configured to retrieve from memory and execute, among other things, instructions related to the control processes and methods described below for the IPG 20. For example, the programmable portion 481 is configured to execute instructions retrieved from the memory 482 for sweeping the electrodes in response to a signal from the CP 22.

The PCB also includes a plurality of additional passive and active components such as resistors, capacitors, inductors, integrated circuits, and amplifiers. These components are arranged and connected to provide a plurality of electrical functions to the PCB including, among other things, filtering, signal conditioning, or voltage regulation, as is commonly known.

Figure 9:
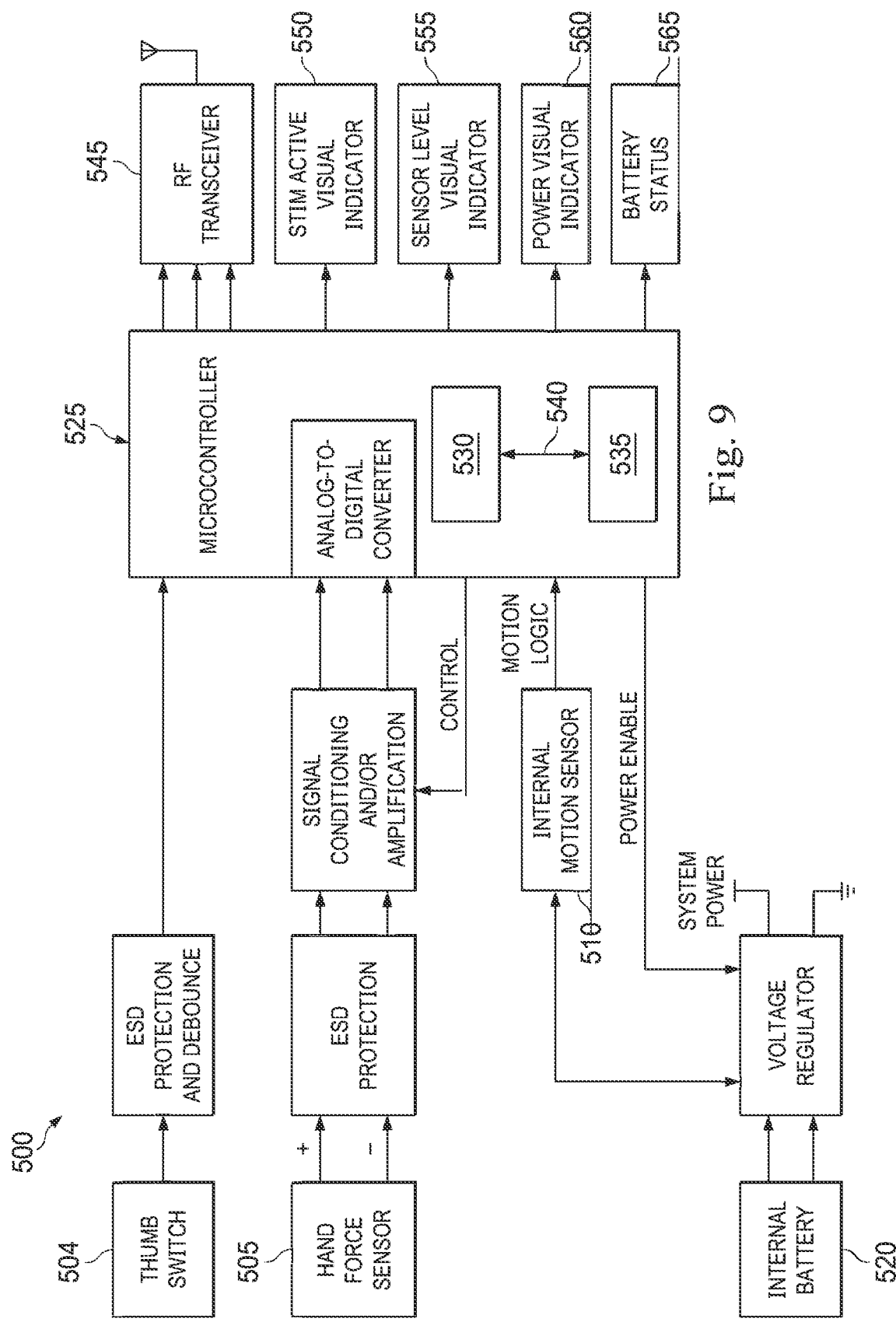
FIG. 9 is a diagrammatic block diagram of a patient feedback device according to an embodiment of the present disclosure.
Figure 10A:
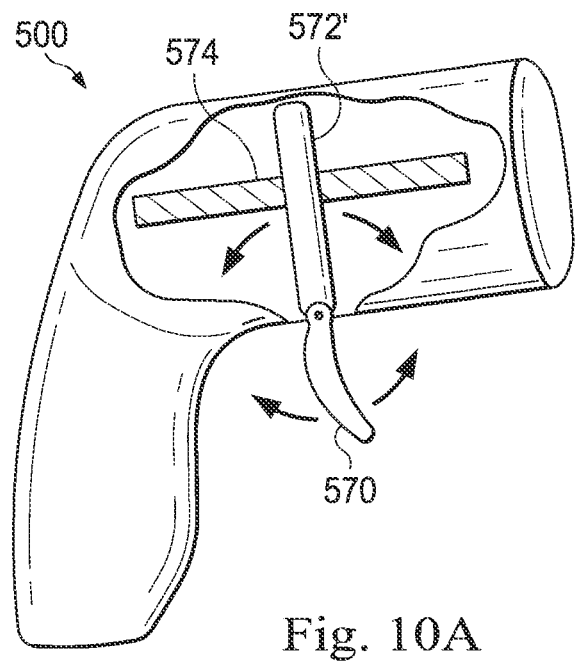
FIGS. 10A and 10B are exterior views of the patient feedback device according to embodiments of the present disclosure.
Figure 10B:
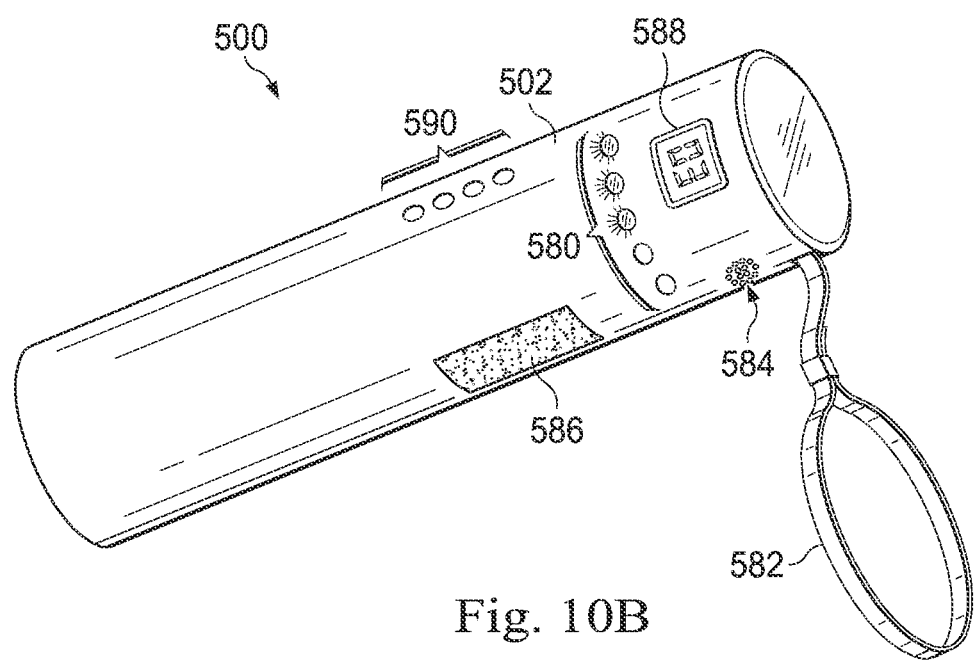

FIG. 9 is a block diagram of an exemplary handheld patient feedback device or patient feedback tool (hereinafter interchangeably referred to as PFD or PFT) 500 for use in a neurostimulation system, and FIGS. 10A and 10B are diagrammatic illustrations of the PFT 500 according to various example embodiments. With reference to FIGS. 9 and 10A-10B, the PFT 500 includes a housing 502 which may have one or more of a sensor, a controller, and/or a communication port connected thereto. The construction of the PFT 500 shown in FIG. 9 includes two inputs 504 and 505 in communication with the housing 502 of the device 500 and one input 510 internal to the housing 502. One of the external inputs 504 is a binary ON/OFF switch, for example activated by the patient's thumb, to allow the patient to immediately deactivate stimulation. Input 504 may be coupled to the controller 525 via electrostatic discharge (ESD) protection and/or debouncing circuits. The second input 505 includes a force sensor sensing the pressure or force exerted by the patient's hand. Input/sensor 505 may be coupled to the controller 525 via ESD protection, signal conditioning, and/or signal amplification circuits. The sensed parameter can be either isotonic (constant force, measuring the distance traversed) or isometric (measured force, proportional to pressure applied by patient). The resulting signal from the sensor 505 is analog and, therefore, after the signal is conditioned and/or amplified, it can be passed to microcontroller 525 via an analog-to-digital converter.

The internal input 510 for the PFT 500 may be a motion sensor. The sensor 510, upon detecting motion, initiates activation of the PFT 500. The device 500 stays active until movement is not detected by the sensor 510 for a time period, which in various constructions may be between one second and five minutes. Power is provided by an internal battery 520 that can be replaceable and/or rechargeable, which in various constructions has an approximately three hour life under continuous use. As discussed below, a motion sensor such as sensor 510 can also be used to obtain feedback from the patient regarding paresthesia.

The processing of the inputs from the sensors 504 and 505 takes place in a controller, such as a microcontroller 525. An exemplary microcontroller capable of being used with the invention is microcontroller 525, which includes a suitable programmable portion 530 (e.g., a microprocessor or a digital signal processor), a memory 535, and a bus 540 or other communication lines. Output data of the microcontroller 525 is sent via a Bluetooth bi-direction radio communication port 545 to the CP (clinician programmer). The Bluetooth portion 545 includes a Bluetooth communication interface, an antenna switch, and a related antenna, all of which allows wireless communication following the Bluetooth Special Interest Group standard. Other forms of wired and wireless communication between the PFT 500 and other components of the system including the CP are also possible. Other outputs may include indicators (such as light-emitting diodes) for communicating stimulation activity 550, sensor activation 555, device power 560, and battery status 565.

The housing 502 of the PFT 500 may be cylindrical in shape, and in one particular construction the cylinder is approximately 35 mm in diameter and 80 mm in length. In other constructions the cylinder is larger or smaller in diameter and/or length, for example in order to accommodate hands of varying sizes. In various constructions the diameter can range from 20 to 50 mm and the length from 30 to 120 mm, although other sizes above and below these ranges are also possible.

Furthermore, the shape of the PFT 500 can be other than a circular cross-section, for example oval, square, hexagonal, or other shape. Still further, the cross-section of the PFT 500 can vary along its length, for example being cylindrical in some portions and oval, square, hexagonal or other shape(s) in other portions. In yet other constructions, the PFT 500 has a spherical, toroid, or other shape.

The housing 502 may be made from a resilient material such as rubber or plastic with one or more sensors 505 coupled to or supported by the housing 502. The manner in which the sensor 505 is coupled to the housing 502 depends on the type of sensor that is employed, as discussed below. Thus, when the patient applies a force to the housing 502, the sensor 505 generates a signal that generally is proportional to the degree of force applied. Although the discussion herein mentions the patient using his or her hand to generate force to squeeze the housing 502 of the PFT 500, in various constructions the patient may instead use other body parts, such as the mouth or foot, to generate force. More generally, the patient can generate feedback by a physical action, usually a force applied by the hand or other body part, but the physical action can include other movements, such as movement of the patient's eyes, head, or hands, to generate a feedback signal.

After the signal is generated, it is transmitted from the sensor 505 to the controller 525. The controller 525 processes the signal and, based on one or more such signals from the sensor 505, the controller 525 generates another signal that is to be transmitted to the CP. The controller 525 sends the signal to be transmitted to the communication port 545 of the PFT 500 from which it is then transmitted to the CP or other external device. As discussed further below, the signal can be transmitted from the communication port 545 to the CP using various wired or wireless methods of communication.

In various constructions, an isotonic force sensor may include a sensor that measures the distance traveled by the sensor with relatively constant force applied by the patient. Isotonic force sensors may include a trigger 570 (See FIG. 10A) or other lever mechanism coupled to a wiper 572 that moves along a rheostat 574 or across a series of detectors. Exemplary detectors include electrical contacts or optical detectors, such as photodiodes. In other constructions, an isometric force sensor may include a strain gauge, a piezoelectric device, or a pressure sensor, each of which measures force that is proportional to the pressure applied to the PFT 500 by the patient, generally with only a small amount of travel or shape change to the sensor.

Both the isotonic and isometric sensors generate an electrical signal that is proportional to the force that is applied to the sensor. An isometric force sensor may be incorporated into a relatively stiff object such that only slight deformation of the object is needed to register a change in force. In still other constructions, the force sensor may include a combination of elements, such as a trigger or other lever that experiences increasing resistance or pressure as the travel distance increases. For example, increasing resistance or pressure can be created by attaching a relatively stiff spring to the lever or wiper mechanism to increase resistance as the lever or wiper is moved.

In some constructions (e.g. as shown in FIG. 10B), the PFT 500 includes a feedback mechanism 580 that indicates to the patient the amount of force that is detected by the force sensor 505. The feedback mechanism 580 may include one or more of a visual, audible, or tactile feedback mechanism that is used to indicate to the patient the degree to which the sensor 505 has been activated, e.g., how much force has been applied or how much the lever or wiper mechanism has traveled. The feedback mechanism gives the patient a sense of whether their activation of the sensor 505 is being detected at what the patient feels is the correct level and to give the patient a means to make their activation of the sensor 505 more consistent.

Visual feedback mechanisms 580 can include a series of lights (e.g. LEDs) or a digital readout (e.g. a numerical display); audible feedback can include sounds that vary in amplitude (volume) and/or tone; and tactile feedback mechanisms can include vibration of the PFT 500 and/or altering the shape of the surface of the PFT 500 (e.g. raising of one or more structures such as dots to form Braille-type patterns) in a location that is capable of contacting the patient's skin. Using a combination of feedback modalities will benefit patients who have sensory impairments, including, e.g., impaired hearing and/or sight.

The feedback can include a semi-quantitative indication of the patient's response, e.g. including a variety of (e.g. 1-5 or 1-10) intensity levels to indicate a relative degree of force applied by the patient. The patient will then be able to see, hear, and/or feel the level of force that is sensed by the sensor 505 of the PFT 500, to help the patient confirm that their response to the stimulus was received, as well as the degree of response that was registered. The correlation between the level of force applied and the output of the feedback mechanism 580 can be calibrated separately for each patient during an initial calibration session.

To facilitate gripping of the PFT 500, the housing 502, in certain constructions, may be covered with one or more surfaces, textures, or materials to improve grip, such as grooves, stipples, indentations, rubber, or plastic, and may include a wrist strap 582 to keep the PFT 500 from falling if it is dropped by the patient.

The PFT 500, in some constructions, may also include a connection feedback mechanism, particularly where the PFT 500 is in wireless communication with the CP. The connection feedback mechanism can include one or more of a visual, audible, or tactile mechanism to inform the patient and/or medical personnel of whether the PFT 500 is maintaining a connection with the CP, the strength of the connection, and/or if the connection has been lost. For example, the PFT 500 may emit a signal (e.g., light, sound, and/or tactile) at regular (e.g., one minute) intervals to confirm that communication is still maintained.

Conversely, the PFT 500 may emit such a signal only if communication is lost. In some constructions, the PFT 500 may tolerate brief intervals in which the signal is lost (e.g., a predetermined time, generally between 0.1-100 sec) before the patient is warned of a possible lost connection. In various constructions, the controller 525 of the PFT 500 includes memory that permits buffering of a limited amount of data, which can be used to accumulate data prior to sending to the CP and which can hold data during brief intervals in which the connection is lost. In various constructions, if communication between the PFT 500 and the CP is lost for more than a predetermined interval of time, then the CP stops stimulation of electrodes until a connection with the PFT 500 is reestablished.

Thus, according to various constructions, the PFT 500 may include one or more of: a sound generating mechanism 584 (e.g., a speaker); a tactile mechanism 586 such as a vibration device and/or a mechanism for creating a raised pattern; a digital numerical readout 588 (e.g., LED or LCD display); and one or more indicator lights 590 (e.g., a series of LEDs); which may be employed to provide feedback to the patient regarding the force being applied and/or communication status.

Various types of sensing mechanisms can be used for the sensor 505, which would depend in part on the type of housing 502 that is used with the PFT 500. For example, if the housing 502 is a sealed, flexible compartment (e.g., a ball or other object filled with gel, air, or liquid) a piezoelectric-based pressure sensing mechanism can be used as the sensor 505 in order to measure changes in pressure when the patient squeezes or relaxes his/her grip on the PFT 500. Alternatively, a rheostat 574 or other linear sensing mechanism can be used with a pistol grip style PFT 500 design (FIG. 10A), where a trigger 570 is coupled to a wiper 572 that moves across the rheostat 574 or other linear sensor.

Figure 11B:
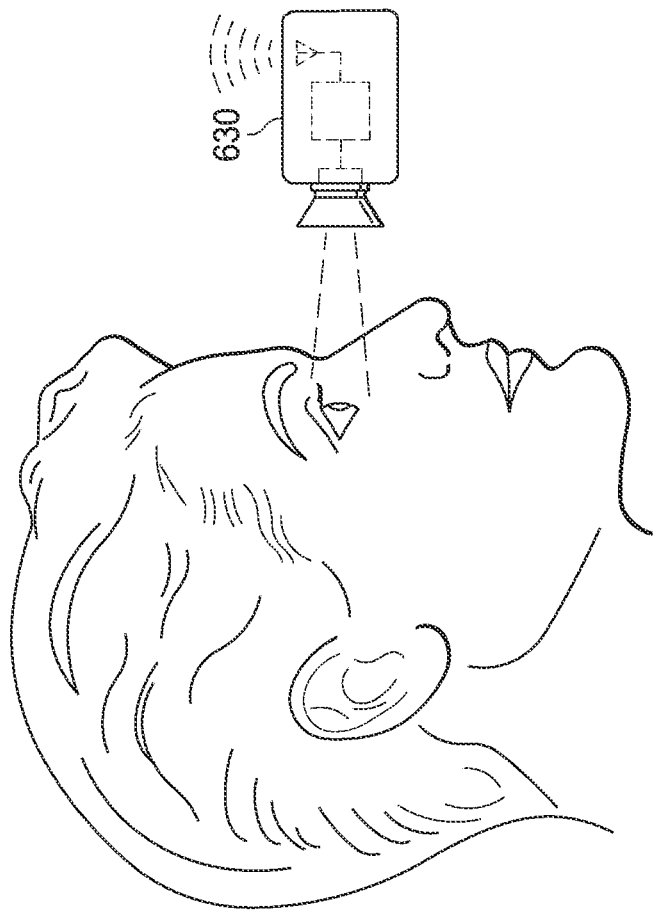
FIG. 11B is a side view of a patient-feedback device with optical sensing according to an embodiment of the present disclosure.
Figure 11A:
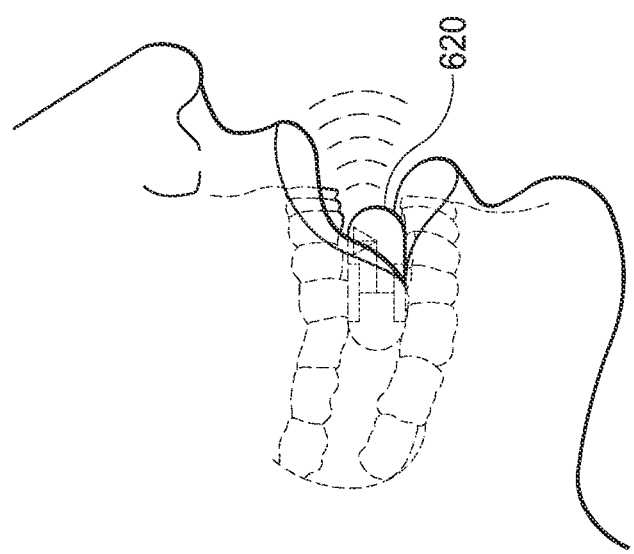
FIG. 11A is a side view of a patient-feedback device inserted in the mouth of a patient according to an embodiment of the present disclosure.
Figure 11C:
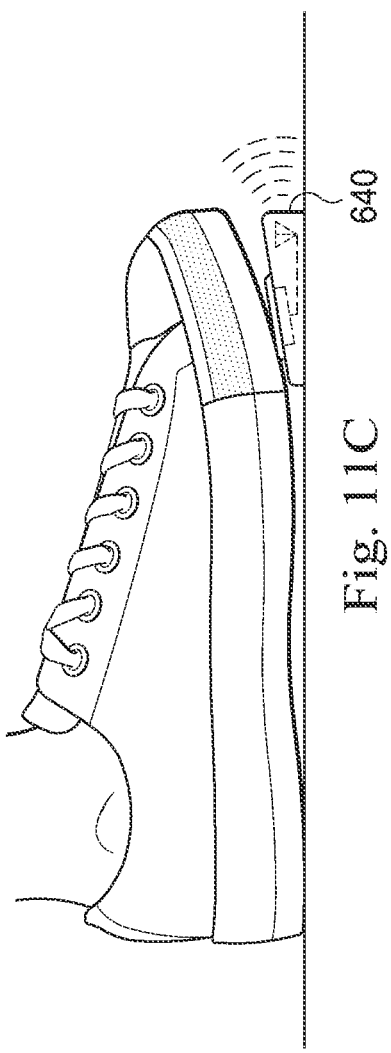
FIG. 11C is a side view of a patient-feedback device activated by a foot of a patient according to an embodiment of the present disclosure.

FIGS. 11A-11C illustrate other embodiments of the PFT for receiving patient feedback. More specifically, FIG. 11A shows a mouth-piece 620 that is inserted into the mouth of the patient. The user provides feedback by biting the mouth-piece. FIG. 11B shows an optical sensor 630 (such as a camera and related image processing software) that detects visual cues from a patient. An example visual cue may be the blinking of the patient's eyes. FIG. 11C shows a foot pedal 640 that receives input through the patient's manipulation of a switch and/or sensor with his foot. In some constructions, the PFT 500 includes one or more accelerometers (such as the motion sensor 510), and the patient provides feedback by moving the PFT 500 in various distinct patterns that are recognized by the controller 525 of the PFT 500 or by the CP.

It is also envisioned that the patient may provide feedback directly to the CP. In various constructions, the patient is trained to use the particular feedback device (e.g. the PFT 500 or the CP as applicable) in order to properly inform the CP of the patient's reaction to stimuli as they are applied to the IPG in the patient. In particular constructions, the CP is programmed to learn the patient's response times and/or the magnitude of the patient's responses in order to obtain a profile of the patient's reaction to various stimuli, as discussed above.

Referring now to FIG. 12, a simplified block diagram of a medical infrastructure 800 (which may also be considered a medical system) is illustrated according to various aspects of the present disclosure. The medical infrastructure 800 includes a plurality of medical devices 810. These medical devices 810 may each be a programmable medical device (or parts thereof) that can deliver a medical therapy to a patient. In some embodiments, the medical devices 810 may include a device of the neurostimulator system discussed above. For example, the medical devices 810 may be a pulse generator (e.g., the IPG discussed above), an implantable lead, a charger, or portions thereof. It is understood that each of the medical devices 810 may be a different type of medical device. In other words, the medical devices 810 need not be the same type of medical device.

The medical infrastructure 800 also includes a plurality of electronic programmers 820. For sake of illustration, one of these electronic programmers 820A is illustrated in more detail and discussed in detail below. Nevertheless, it is understood that each of the electronic programmers 820 may be implemented similar to the electronic programmer 820A.

In some embodiments, the electronic programmer 820A may be a clinician programmer, for example the clinician programmer discussed above with reference to FIGS. 2B and 7. In other embodiments, the electronic programmer 820A may be a patient programmer discussed above with reference to FIGS. 2B-6. In further embodiments, it is understood that the electronic programmer may be a tablet computer. In any case, the electronic programmer 820A is configured to program the stimulation parameters of the medical devices 810 so that a desired medical therapy can be delivered to a patient.

The electronic programmer 820A contains a communications component 830 that is configured to conduct electronic communications with external devices. For example, the communications device 830 may include a transceiver. The transceiver contains various electronic circuitry components configured to conduct telecommunications with one or more external devices. The electronic circuitry components allow the transceiver to conduct telecommunications in one or more of the wired or wireless telecommunications protocols, including communications protocols such as IEEE 802.11 (Wi-Fi), IEEE 802.15 (Bluetooth), GSM, CDMA, LTE, WIMAX, DLNA, HDMI, Medical Implant Communication Service (MICS), etc. In some embodiments, the transceiver includes antennas, filters, switches, various kinds of amplifiers such as low-noise amplifiers or power amplifiers, digital-to-analog (DAC) converters, analog-to-digital (ADC) converters, mixers, multiplexers and demultiplexers, oscillators, and/or phase-locked loops (PLLs). Some of these electronic circuitry components may be integrated into a single discrete device or an integrated circuit (IC) chip.

The electronic programmer 820A contains a touchscreen component 840. The touchscreen component 840 may display a touch-sensitive graphical user interface that is responsive to gesture-based user interactions. The touch-sensitive graphical user interface may detect a touch or a movement of a user's finger(s) on the touchscreen and interpret these user actions accordingly to perform appropriate tasks. The graphical user interface may also utilize a virtual keyboard to receive user input. In some embodiments, the touch-sensitive screen may be a capacitive touchscreen. In other embodiments, the touch-sensitive screen may be a resistive touchscreen.

It is understood that the electronic programmer 820A may optionally include additional user input/output components that work in conjunction with the touchscreen component 840 to carry out communications with a user. For example, these additional user input/output components may include physical and/or virtual buttons (such as power and volume buttons) on or off the touch-sensitive screen, physical and/or virtual keyboards, mouse, track balls, speakers, microphones, light-sensors, light-emitting diodes (LEDs), communications ports (such as USB or HDMI ports), joy-sticks, etc.

The electronic programmer 820A contains an imaging component 850. The imaging component 850 is configured to capture an image of a target device via a scan. For example, the imaging component 850 may be a camera in some embodiments. The camera may be integrated into the electronic programmer 820A. The camera can be used to take a picture of a medical device, or scan a visual code of the medical device, for example its barcode or Quick Response (QR) code.

The electronic programmer contains a memory storage component 860. The memory storage component 860 may include system memory, (e.g., RAM), static storage (e.g., ROM), or a disk drive (e.g., magnetic or optical), or any other suitable types of computer readable storage media. For example, some common types of computer readable media may include floppy disk, flexible disk, hard disk, magnetic tape, any other magnetic medium, CD-ROM, any other optical medium, RAM, PROM, EPROM, FLASH-EPROM, any other memory chip or cartridge, or any other medium from which a computer is adapted to read. The computer readable medium may include, but is not limited to, non-volatile media and volatile media. The computer readable medium is tangible, concrete, and non-transitory. Logic (for example in the form of computer software code or computer instructions) may be encoded in such computer readable medium. In some embodiments, the memory storage component 860 (or a portion thereof) may be configured as a local database capable of storing electronic records of medical devices and/or their associated patients.

The electronic programmer contains a processor component 870. The processor component 870 may include a central processing unit (CPU), a graphics processing unit (GPU) a micro-controller, a digital signal processor (DSP), or another suitable electronic processor capable of handling and executing instructions. In various embodiments, the processor component 870 may be implemented using various digital circuit blocks (including logic gates such as AND, OR, NAND, NOR, XOR gates, etc.) along with certain software code. In some embodiments, the processor component 870 may execute one or more sequences computer instructions contained in the memory storage component 860 to perform certain tasks.

It is understood that hard-wired circuitry may be used in place of (or in combination with) software instructions to implement various aspects of the present disclosure. Where applicable, various embodiments provided by the present disclosure may be implemented using hardware, software, or combinations of hardware and software. Also, where applicable, the various hardware components and/or software components set forth herein may be combined into composite components comprising software, hardware, and/or both without departing from the spirit of the present disclosure. Where applicable, the various hardware components and/or software components set forth herein may be separated into sub-components comprising software, hardware, or both without departing from the scope of the present disclosure. In addition, where applicable, it is contemplated that software components may be implemented as hardware components and vice-versa.

It is also understood that the electronic programmer 820A is not necessarily limited to the components 830-870 discussed above, but it may further include additional components that are used to carry out the programming tasks. These additional components are not discussed herein for reasons of simplicity. It is also understood that the medical infrastructure 800 may include a plurality of electronic programmers similar to the electronic programmer 820A discussed herein, but they are not illustrated in FIG. 12 for reasons of simplicity.

The medical infrastructure 800 also includes an institutional computer system 890. The institutional computer system 890 is coupled to the electronic programmer 820A. In some embodiments, the institutional computer system 890 is a computer system of a healthcare institution, for example a hospital. The institutional computer system 890 may include one or more computer servers and/or client terminals that may each include the necessary computer hardware and software for conducting electronic communications and performing programmed tasks. In various embodiments, the institutional computer system 890 may include communications devices (e.g., transceivers), user input/output devices, memory storage devices, and computer processor devices that may share similar properties with the various components 830-870 of the electronic programmer 820A discussed above. For example, the institutional computer system 890 may include computer servers that are capable of electronically communicating with the electronic programmer 820A through the MICS protocol or another suitable networking protocol.

The medical infrastructure 800 includes a database 900. In various embodiments, the database 900 is a remote database—that is, located remotely to the institutional computer system 890 and/or the electronic programmer 820A. The database 900 is electronically or communicatively (for example through the Internet) coupled to the institutional computer system 890 and/or the electronic programmer. In some embodiments, the database 900, the institutional computer system 890, and the electronic programmer 820A are parts of a cloud-based architecture. In that regard, the database 900 may include cloud-based resources such as mass storage computer servers with adequate memory resources to handle requests from a variety of clients. The institutional computer system 890 and the electronic programmer 820A (or their respective users) may both be considered clients of the database 900. In certain embodiments, the functionality between the cloud-based resources and its clients may be divided up in any appropriate manner. For example, the electronic programmer 820A may perform basic input/output interactions with a user, but a majority of the processing and caching may be performed by the cloud-based resources in the database 900. However, other divisions of responsibility are also possible in various embodiments.

According to the various aspects of the present disclosure, various types of data may be uploaded from the electronic programmer 820A to the database 900. The data saved in the database 900 may thereafter be downloaded by any of the other electronic programmers 820B-820N communicatively coupled to it, assuming the user of these programmers has the right login permissions.

The database 900 may also include a manufacturer's database in some embodiments. It may be configured to manage an electronic medical device inventory, monitor manufacturing of medical devices, control shipping of medical devices, and communicate with existing or potential buyers (such as a healthcare institution). For example, communication with the buyer may include buying and usage history of medical devices and creation of purchase orders. A message can be automatically generated when a client (for example a hospital) is projected to run out of equipment, based on the medical device usage trend analysis done by the database. According to various aspects of the present disclosure, the database 900 is able to provide these functionalities at least in part via communication with the electronic programmer 820A and in response to the data sent by the electronic programmer 820A. These functionalities of the database 900 and its communications with the electronic programmer 820A will be discussed in greater detail later.

The medical infrastructure 800 further includes a manufacturer computer system 910. The manufacturer computer system 910 is also electronically or communicatively (for example through the Internet) coupled to the database 900. Hence, the manufacturer computer system 910 may also be considered a part of the cloud architecture. The computer system 910 is a computer system of medical device manufacturer, for example a manufacturer of the medical devices 810 and/or the electronic programmer 820A.

In various embodiments, the manufacturer computer system 910 may include one or more computer servers and/or client terminals that each includes the necessary computer hardware and software for conducting electronic communications and performing programmed tasks. In various embodiments, the manufacturer computer system 910 may include communications devices (e.g., transceivers), user input/output devices, memory storage devices, and computer processor devices that may share similar properties with the various components 830-870 of the electronic programmer 820A discussed above. Since both the manufacturer computer system 910 and the electronic programmer 820A are coupled to the database 900, the manufacturer computer system 910 and the electronic programmer 820A can conduct electronic communication with each other.

After an implantable lead (e.g., lead 10 discussed above with reference to FIGS. 2A-2B) has been placed inside the patient, an electronic programmer (e.g., the clinician programmer 22 discussed above with reference to FIG. 7) may be used to program a pulse generator (e.g., IPG 20 discussed above with reference to FIG. 8) to deliver electrical stimulation to the patient through the lead. According to the various aspects of the present disclosure, the pulse generator herein is capable of generating a unique stimulation waveform. For example, unlike conventional neurostimulation waveforms that have periodic pulses (e.g., at a fixed frequency), the pulse generator of the present disclosure can generate a stimulation waveform 1000 that has a paresthesia-inducing low-frequency component and a spread-spectrum non-paresthesia inducing high-frequency component. These components are illustrated in both FIG. 13 and FIG. 14 below, where FIG. 13 illustrates a portion of the waveform 1000 in a time domain, and FIG. 14 illustrates a portion of the waveform 1000 in a frequency domain.

Figure 13:
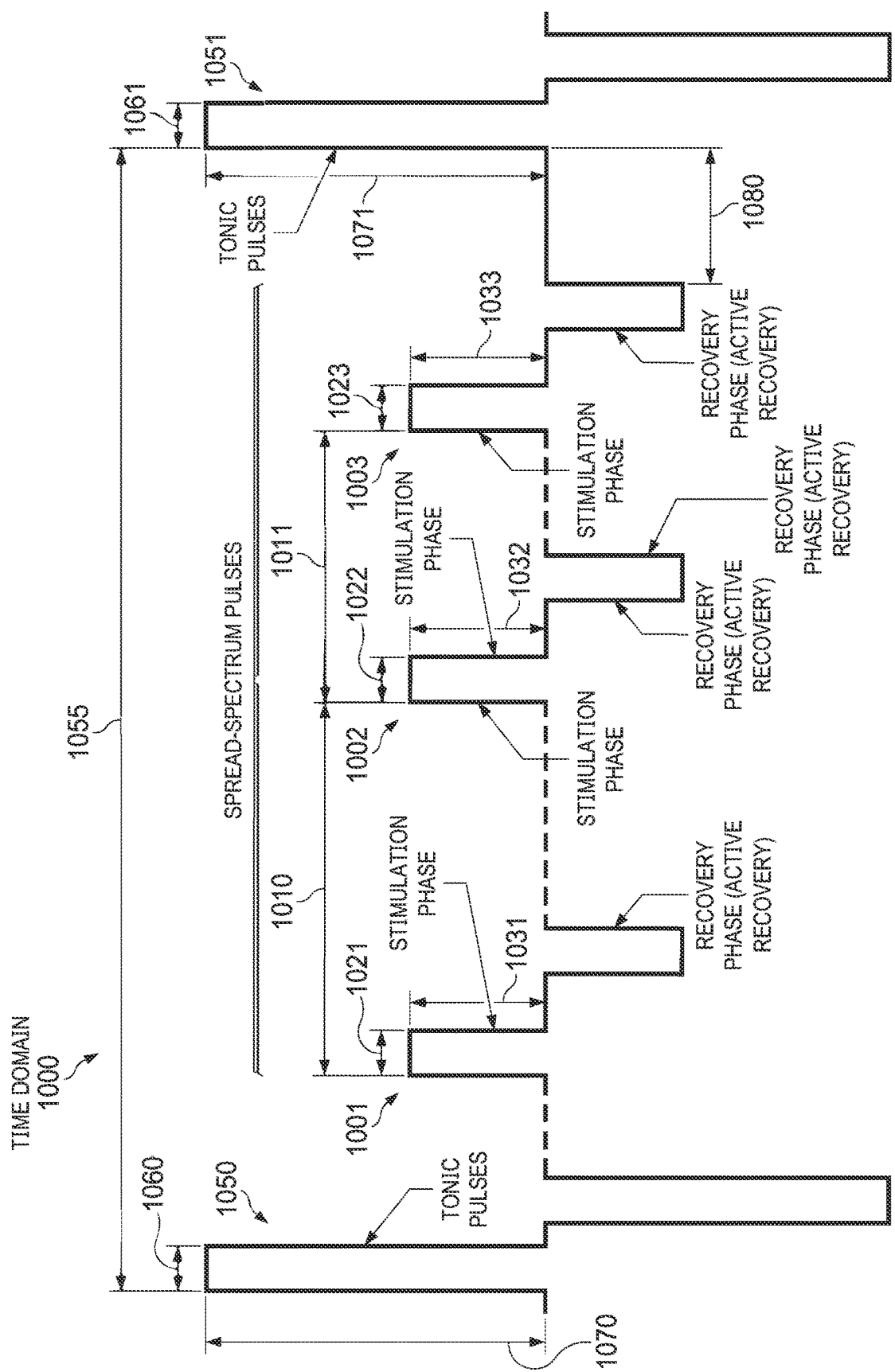
FIG. 13 is an illustration of a portion of a stimulation waveform generated by a pulse generator in a time domain according to various aspects of the present disclosure.
Figure 14:
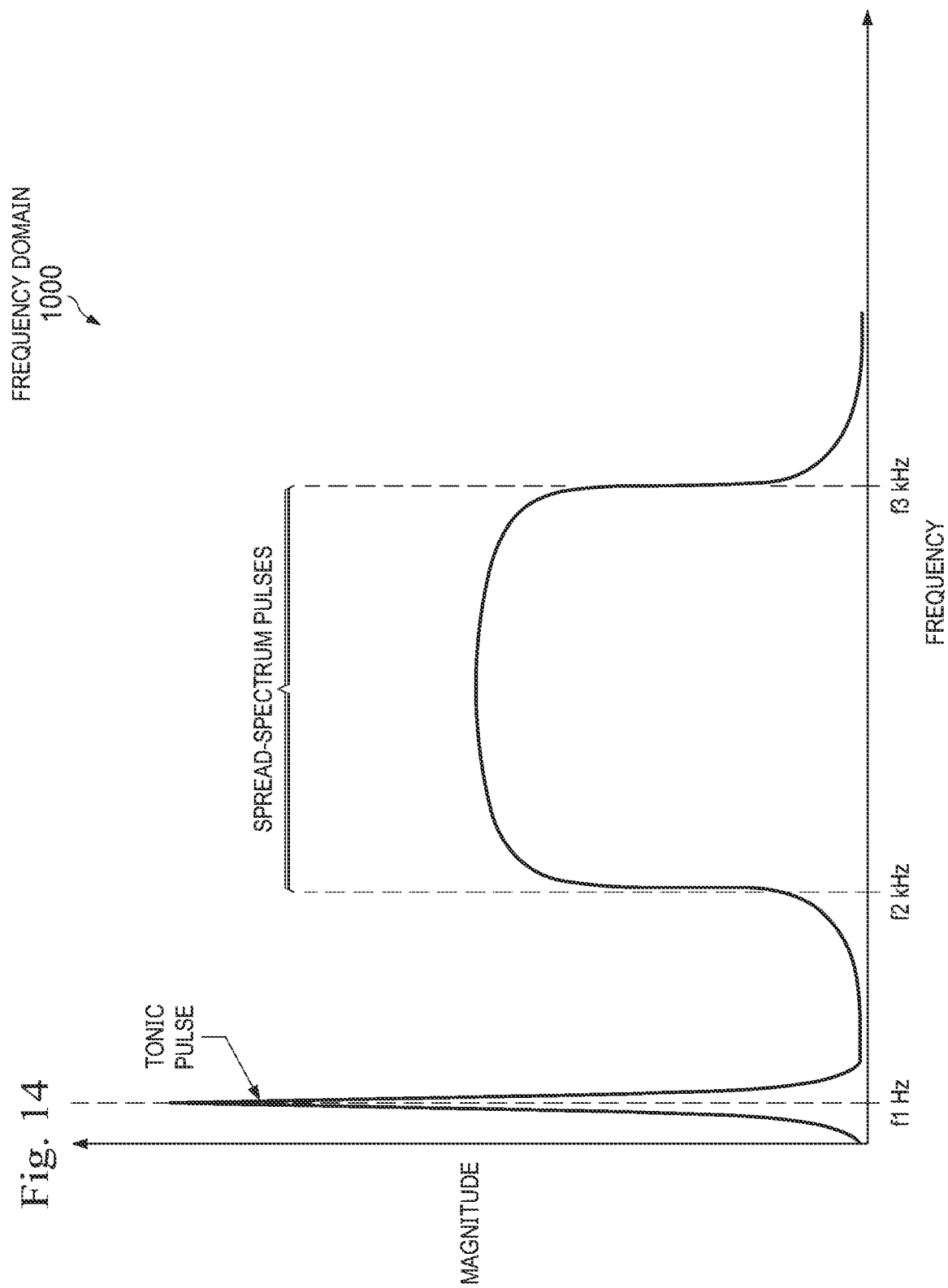
FIG. 14 is an illustration of the stimulation waveform of FIG. 13 in a frequency domain according to various aspects of the present disclosure.

Referring to FIG. 13, three example spread-spectrum pulses (also referred to as sub-tonic pulses) are illustrated in the time domain as spread-spectrum pulses 1001, 1002, and 1003, where of the pulses each have a respective stimulation phase and a respective recovery phase. The recovery phases are shown as being active recovery, but passive recovery is also possible. In addition, although each of the spread-spectrum pulses has its own recovery phase in the embodiment of FIG. 13, it is understood that multiple spread-spectrum pulses may collectively have a single recovery phase in other embodiments. For example, if there are 20 spread-spectrum pulses between a pair of tonic pulses, the 20 spread-spectrum pulses may have a single recovery phase (which may be active recovery or passive recovery) after the active stimulation phase for all 20 of the spread-spectrum pulses has occurred, or there may be a first recovery phase after the stimulation phase for the first 10 of the 20 spread-spectrum pulses has occurred, and a second recovery phase after the stimulation phase for the second 10 of the 20 spread-spectrum pulses has occurred, or there may be a recovery phase after the occurrence of the stimulation phase for each of the 20 spread-spectrum pulses.

The spread-spectrum nature of the pulses may manifest itself as jitter in the time domain. For example, the periods between pulses are not constant, but they have varying values. A period may be defined as the amount of elapsed time between the rising edges of adjacent pulses in the stimulation phase (or alternatively, the falling edges of adjacent pulses in the stimulation phase). In this example, a period (e.g., a time interval) 1010 between pulses 1001 and 1002 is different in value from a period 1011 between pulses 1002 and 1003. For example, the period 1010 may have a value of 0.2 milli-seconds (ms), while the period 1011 may have a value of 0.15 ms. Of course, these values are merely examples, and it is understood that other values are implemented in different embodiments. In addition, although the elements 1010 and 1011 are each referred to as "period" or "time period", it is understood that they do not have a periodic occurrence or pattern, as discussed in more detail below.

In some embodiments, the varying of the time periods (e.g., the periods 1010 and 1011) between adjacent spread-spectrum pulses is performed using a pseudo-random number generator, which could be a module inside the IPG 20 or alternatively in the clinician programmer 22. Based on one or more seed values, the pseudo-random number generator is configured to generate a series of pseudo-random values whose properties approximate the properties of sequences of truly random numbers. In some embodiments, the series of pseudo-random values are in a predefined range, for example in a range between X and Y, where X and Y are values corresponding to the time period (e.g., the period 1010) between two adjacent spread spectrum pulses. In this manner, after one of the spread spectrum pulses is generated, the pulse generator 20 has to "wait" an amount of time—specified according to the output of the pseudo-random number generator—before generating the subsequent spread spectrum pulse. The varying time periods of the spread-spectrum pulses correspond to a spreading in the frequency spectrum or frequency domain, which is shown in FIG. 14 and discussed below in more detail.

Still referring to FIG. 13, the example spread-spectrum pulses 1001, 1002, and 1003 have their respective pulse widths 1021, 1022, and 1023. In some embodiments, the pulse widths 1021, 1022, and 1023 are equal to one another. In other embodiments, the pulse widths 1021, 1022, and 1023 may be configured to have different values too. The example spread-spectrum pulses 1001, 1002, and 1003 have their respective stimulation amplitudes 1031, 1032, and 1033. In some embodiments, the amplitudes 1031, 1032, and 1033 are equal to one another. In other embodiments, the amplitudes 1031, 1032, and 1033 may be configured to have different values too. The spread-spectrum pulses 1001-1003 are configured to not cause paresthesia. Paresthesia may refer to a tingling or a numbing sensation felt by the patient in response to electrical stimulation, and in some cases paresthesia may mask pain, thereby leading to therapeutic relief. In some embodiments, the spread-spectrum pulses 1001-1003 have sufficiently narrow pulse widths 1021-1023, and/or sufficiently low stimulation amplitudes 1031-1033, such that the application of the pulses 1001-1003 does not recruit the deep nerve fibers that are needed to cause paresthesia. This is also referred to as sub-threshold stimulation. In some embodiments, the pulse width of the spread-spectrum pulses 1001-1003 has a range between about 1 microsecond and about 10,000 microseconds.

Still referring to FIG. 13, the stimulation waveform 1000 also includes paresthesia-inducing pulses (also referred to as "tonic pulses" interchangeably hereinafter), two example of which are illustrated as pulses 1050-1051 herein. The paresthesia-inducing pulses 1050-1051 occur periodically at a fixed frequency that is substantially lower than the frequency range of the spread-spectrum pulses 1001-1003. For example, the tonic pulses 1050-1051 have a period of 1055, which is fixed between any two adjacent tonic pulses for a given stimulation waveform. Of course, the frequency (and the period 1055) of the tonic pulses may be programmed (as a programmable stimulation parameter) to change from waveform to waveform. But for any given waveform, the tonic pulses have a fixed frequency (and a fixed period 1055 between pulses). Again, this is in contrast with the spread-spectrum pulses 1001-1003, which have varying frequencies and periods even within a given stimulation waveform. The programming of the stimulation waveforms is described in more detail in U.S. Pat. No. 9,471,753, which was filed on Aug. 31, 2012, issued on Oct. 18, 2016, and entitled "Programming And Virtual Reality Representation Of Stimulation Parameter Groups," the disclosure of which is hereby incorporated by reference in its entirety. In some embodiments, a given stimulation waveform corresponds to a stimulation program discussed in U.S. Pat. No. 9,471,753. For example, during the execution of a certain stimulation program—with its various stimulation parameters (e.g., stimulation amplitude, frequency, pulse width) specified by a programmer—the stimulation program will produce a given stimulation waveform, which according to the present disclosure may include both the spread-spectrum pulses that have no fixed frequency, as well as the tonic pulses that have a fixed frequency.

In some embodiments, the frequency of the tonic pulses 1050-1051 is at least an order of magnitude (e.g., 10 times) lower than the frequency range of the spread-spectrum pulses 1001-1003. For example, in embodiments where the frequencies of the spread-spectrum pulses 1001-1003 are in the kilo-Hertz (kHz) range, the tonic pulses 1050-1051 have a frequency range of between 20 Hz and 700 Hz, for example a frequency of 60 pulses per second (60 Hz). In other embodiments, the tonic pulses 1050-1051 have a frequency that is in the tens of Hz or in the hundreds of Hz.

The tonic pulses 1050-1051 have pulse widths 1060 and 1061, respectively. The tonic pulses 1050-1051 also have stimulation amplitudes 1070 and 1071, respectively. The pulse widths 1060-1061 and/or the stimulation amplitudes 1070-1071 of the tonic pulses 1050-1051 are configured so that the tonic pulses 1050-1051 cause comfortable paresthesia in the target patient to whom the stimulation waveform 1000 is applied as a part of neurostimulation therapy. In order to produce paresthesia, the tonic pulses 1050-1051 need to deliver enough energy to recruit deeper nerve fibers than what the spread-spectrum pulses 1001-1003 can recruit. As such, the pulse widths 1060-1061 and/or the stimulation amplitudes 1070-1071 need to be configured to sufficiently large to deliver such energy. Compared to the spread-spectrum pulses 1001-1003, the tonic pulses 1050-1051 may have either much greater pulse widths, or much greater stimulation amplitudes, or both. In some embodiments, the pulse width of each of the tonic pulses 1050-1051 is in a range between about 1 microsecond and about 10,000 microseconds. The pulse width and the frequency of the tonic stimulation will determine an available gap (e.g., time period in which the spread-spectrum pulses may occur) for the spread-spectrum stimulation (also referred to as spectral stimulation).

Due to the much lower frequency of the paresthesia-inducing tonic pulses, there may be many spread-spectrum pulses 1001-1003 between two adjacent tonic pulses 1050-1051. Due the space limitations, FIG. 13 illustrates only three of the spread-spectrum pulses 1001-1003 as examples, but it is understood that there may be several tens (or even hundreds) of the spread-spectrum pulses between each adjacent pair of tonic pulses. The exact number of the spread-spectrum pulses between each adjacent pair of the tonic pulses may vary as well, due to the pseudo-random nature of the frequency of the spread-spectrum pulses. In other words, there may be an M number of spread-spectrum pulses between one adjacent pair of the tonic pulses, but there may be an N number of spread-spectrum pulses between another adjacent pair of the tonic pulses.

Another important characteristic of the stimulation waveform 1000 is that there is a predefined "refractory interval" between the start of a paresthesia-inducing tonic pulse and the end of the recovery phase of a preceding spread-spectrum pulse. For example, FIG. 13 illustrates an example refractory interval 1080 between the start of the active stimulation phase of the tonic pulse 1051 and the end of the recovery phase for the preceding spread-spectrum pulse 1003. The refractory interval 1080 has to be sufficiently long, so as to allow the neurons (that have been stimulated by the high-frequency spread-spectrum pulses preceding the tonic pulse) to depolarize so that they can be repolarized by the tonic pulse 1051.

Referring to FIG. 14, a frequency domain plot of the stimulation waveform 1000 is illustrated. The time-domain-to-frequency-domain transformation may be done via a Fourier Transform, for example. The X-axis represents frequency (e.g., frequency of the pulses of the stimulation waveform), and the Y-axis represents magnitude (e.g., magnitude of the pulses of the stimulation waveform, which may be in decibels, or in a logarithmic scale). In some embodiments, FIG. 14 illustrates the amount of energy occupying each frequency band.

As FIG. 14 clearly shows, the paresthesia-inducing component (i.e., the tonic pulses 1050-1051 shown in FIG. 13) of the stimulation waveform 1000 manifests itself as a very "narrow" pulse (with a center frequency) in the frequency domain, whereas the spread-spectrum component of the stimulation waveform 1000 occupies a much "wider" frequency range (hence, the name "spread-spectrum"). The paresthesia-inducing component has a much lower center frequency of f1 Hz, and the spread-spectrum component has a much higher frequency range, which is between f2 kHz and f3 kHz. For example, f1 may be 60, f2 may be 6, and f3 may be 8. In other words, the frequency of the spread-spectrum pulses may be several orders of magnitude higher than the frequency of the paresthesia-inducing tonic pulses.

Figure 15:
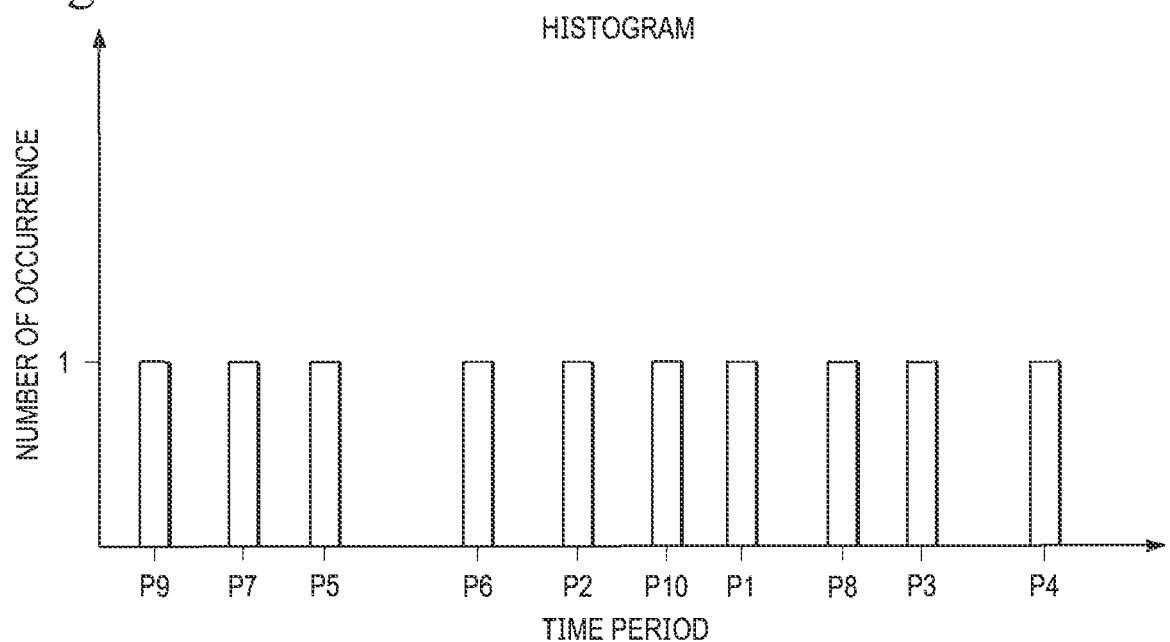
FIGS. 15-16 illustrate histograms associated with a stimulation waveform according to various aspects of the present disclosure.

In some embodiments, the spread spectrum pulses are configured such that the frequencies of the spread spectrum pulses are continuously changing and do not repeat. For example, although a plurality of spread spectrum pulses exist between two adjacent tonic pulses, none of these spread spectrum pulses will have the same frequency, which means that the time period between any two of the spread spectrum pulses is never equal to another time period between any of the two other spread spectrum pulses. A simplified example of this embodiment is shown in FIG. 15, which illustrates a histogram of a number of occurrences for different time periods of the spread spectrum pulses. The X-axis represents the time period, for example a time period (e.g., similar to the periods 1010 or 1011 of FIG. 13) between any two adjacent spread spectrum pulses. The Y-axis represents the number of occurrences associated with each unique time period.

As shown in FIG. 15, a histogram of time periods P1-P10 is illustrated. In one example, P1 represents a time period between a first spread spectrum pulse (e.g., 1001 of FIG. 13) and a second spread spectrum pulse (e.g., 1002 of FIG. 13), P2 represents a time period between the second spread spectrum pulse and a third spread spectrum pulse, P3 represents a time period between the third spread spectrum pulse and a fourth spread spectrum pulse, P4 represents a time period between the fourth spread spectrum pulse and a fifth spread spectrum pulse, so on and so forth, such that P10 represents a time period between the tenth spread spectrum pulse and an eleventh spread spectrum pulse (e.g., 1003 of FIG. 13). In some embodiments, the first spread spectrum pulse is located adjacent to the second spread spectrum pulse, the second spread spectrum pulse is located adjacent to the third spread spectrum pulse, the third spread spectrum pulse is located adjacent to the fourth spread spectrum pulse, so on and so forth, such that the tenth spread spectrum pulse is located adjacent to the eleventh spread spectrum pulse. As the histogram in FIG. 15 indicates, each of the time periods P1-P10 only has a single occurrence, meaning that no time periods are repeated (or no two time periods of the spread spectrum pulses are the same). For the sake of providing a non-limiting numerical example, P1 may be 0.2 ms, P2 may be 0.19 ms, P3 may be 0.22 ms, P4 may be 0.23 ms, P5 may be 0.18 ms, P6 may be 0.185 ms, P7 may be 0.177 ms, P8 may be 0.21 ms, P9 may be 0.16 ms, and P10 may be 0.195 ms. Again, none of the two periods are the same, which means no period occurs more than once.

In some embodiments, not only are the periods between adjacent spread spectrum pulses non-repeating, but the same is true for periods between non-adjacent spread spectrum pulses as well. For example, referring to FIG. 16, an expanded histogram is illustrated. The expanded histogram illustrates time periods P11-P13, as an example subset of the time periods between non-adjacent pulses. For example, P11 may represent the time period between the first pulse and the third pulse, P12 may represent the time period between the first pulse and the fifth pulse, and P13 may represent the time period between the third pulse and the ninth pulse. Again, it can be seen that P11 is different from P1-P10 and P12-P13, P12 is different from P1-P11, and P13, and P13 is different from P1-P12, and they each have an occurrence of 1. Since there are many more permutations of different pulses between which a period time can be defined, it is understood that FIG. 16 merely shows an incomplete subset of all the possible time periods corresponding to the different possible permutations, for reasons of simplicity. Nevertheless, in the embodiment represented by FIG. 16, none of the possible time periods will have an occurrence more than 1, meaning that there is no repeating time pattern associated with the spread spectrum pulses, which are completely randomized.

Figure 16:
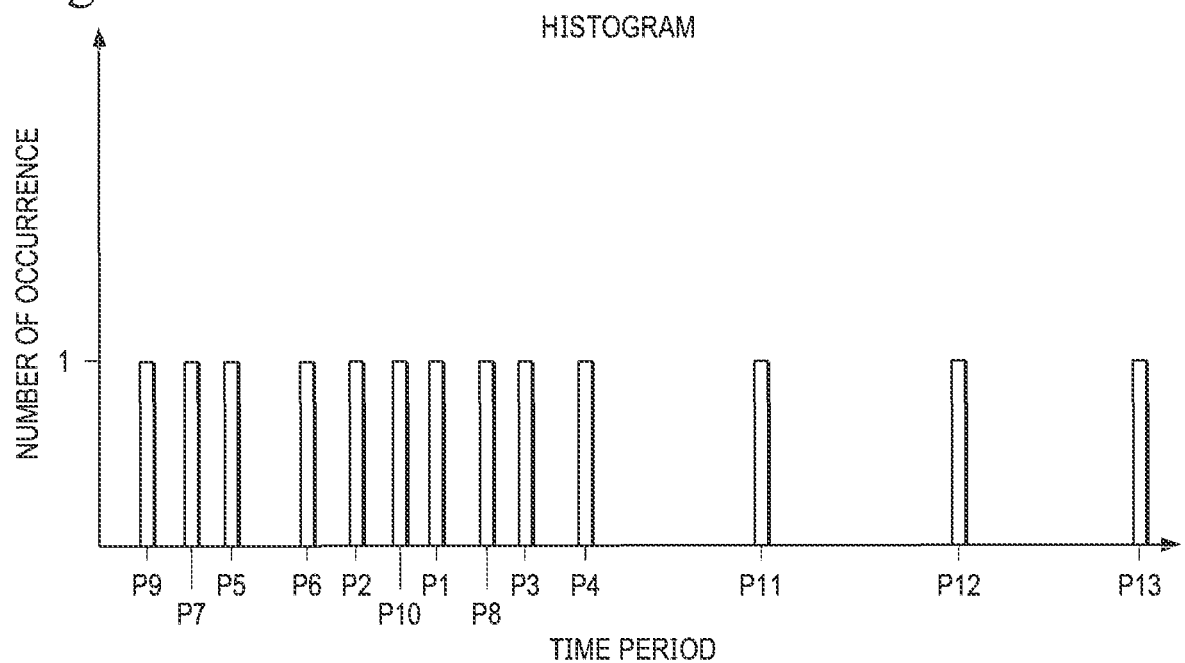

In the embodiments corresponding to FIGS. 15-16, the time periods P1-13 are associated with spread spectrum pulses between two adjacent tonic pulses (e.g., between the tonic pulses 1050-1051 of FIG. 13). In other words, within a given time period (e.g., the period 1055 of FIG. 13) of the tonic pulses, the time periods of spread spectrum pulses therein are randomized and non-repeating. In other embodiments, this implementation may extend to multiple time periods of the tonic pulses as well. For example, between a first tonic pulse and a fifth tonic pulse—which spans a time period of four tonic pulse periods—none of the time periods between the spread spectrum pulses has more than a single occurrence. Such a randomized implementation of the spread spectrum pulses may help prevent habituation, which is a benefit of the present disclosure disclosed below.

Figure 17:
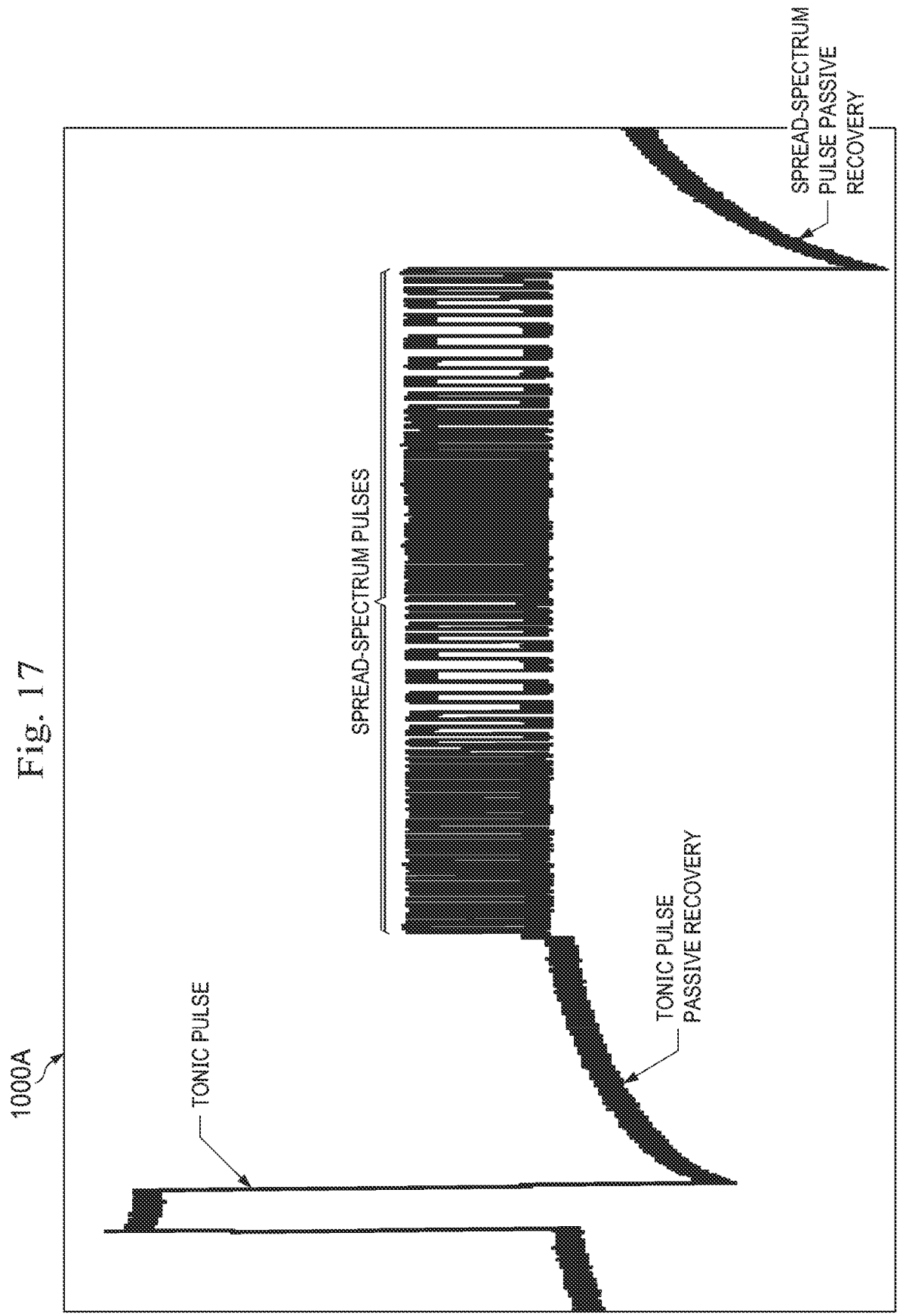
FIG. 17 illustrates an example stimulation waveform in a time domain according to various aspects of the present disclosure.

FIG. 17 illustrates a more realistic example of the stimulation waveform having a low frequency tonic component and a high frequency spread spectrum component. For example, a stimulation waveform 1000A is illustrated as a non-limiting example embodiment of the stimulation waveform 1000 discussed above. The stimulation waveform 1000A is shown in a time domain, for example as a captured waveform from an oscilloscope. As shown in FIG. 17, the stimulation waveform 1000A includes a tonic pulse followed by a plurality of spread-spectrum pulses. The tonic pulse may be similar to the pulse 1050 of FIG. 13, and the spread-spectrum pulses may be similar to the pulses 1001-1003 of FIG. 13. For example, the tonic pulse has a substantially lower frequency than the spread-spectrum pulses, but it has a greater amplitude and a longer pulse width than each of the spread-spectrum pulses. In addition, as discussed above with reference to FIG. 13, though the tonic pulse has a fixed frequency, the spread-spectrum pulses have no fixed frequency (for a given duration of time), which is evidenced in FIG. 17 by the fact that the time intervals separating the spread-spectrum pulses are constantly changing and do not remain fixed.

One difference between the stimulation waveforms 1000 and 1000A is that, unlike the pulses in FIG. 13—which have active recoveries—the tonic pulse of the stimulation waveform 1000A has a passive recovery portion following an active stimulation portion, and that the spread-spectrum pulses collectively have a passive recovery portion following a plurality of active stimulation pulses. In other embodiments, active recoveries may be implemented for the tonic pulse and/or the spread-spectrum pulses in a manner similar to the stimulation waveform 1000 discussed above with reference to FIG. 13. In addition, a passive recovery may be implemented for each spread-spectrum pulse, rather than a single recovery for a plurality of spread-spectrum pulse, as shown in FIG. 17.

Figure 18:
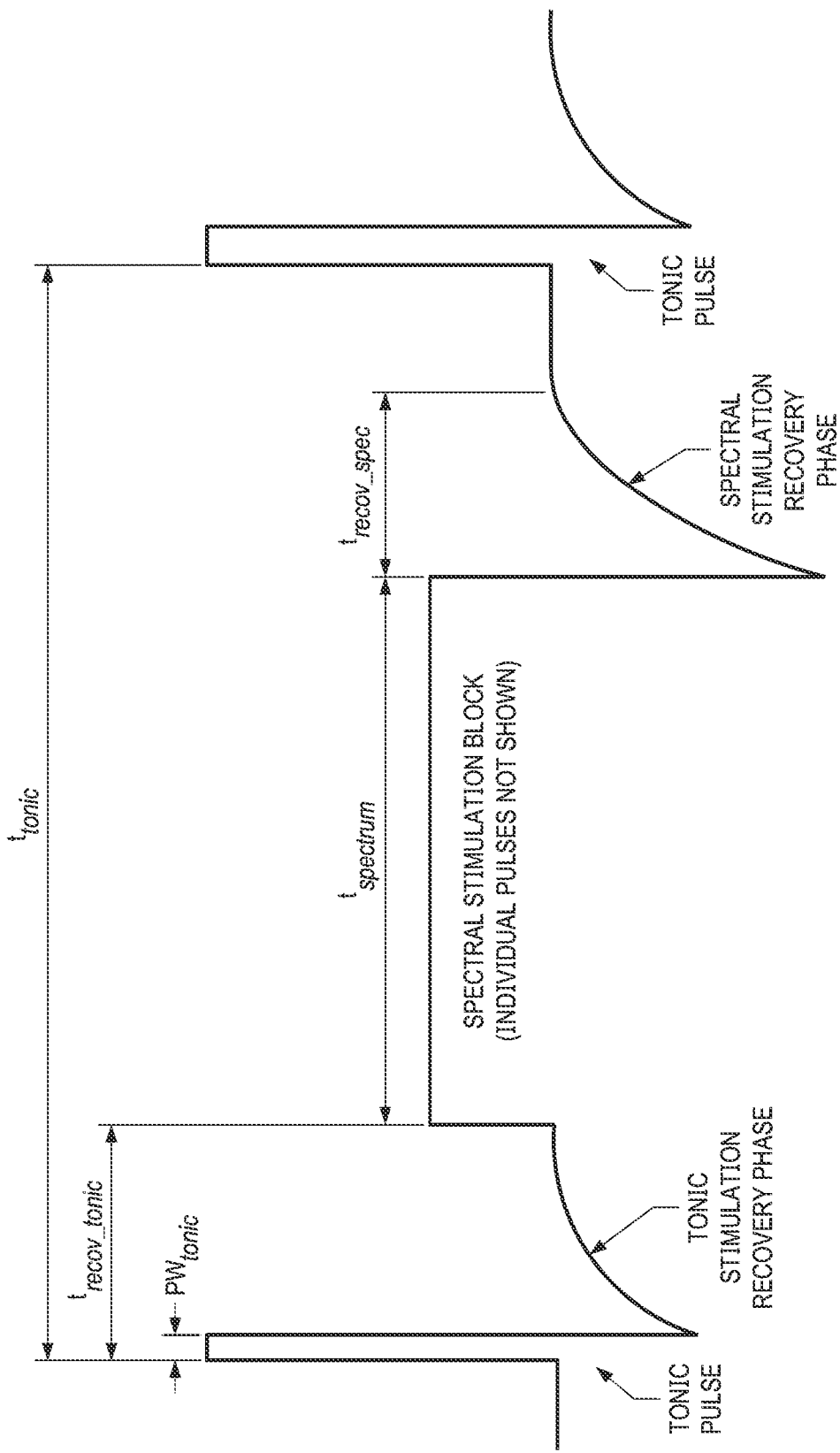
FIG. 18 illustrates a simplified example stimulation waveform without a spread-spectrum stimulation component in a time domain according to various aspects of the present disclosure.

FIG. 18 is a simplified example stimulation waveform without the spread-spectrum stimulation component (also referred to as spectral stimulation) in a time domain according to various aspects of the present disclosure. The omission of the spread-spectrum component does not mean that the spread-spectrum component is missing in the actual waveform, but that it is just not shown in FIG. 18 for reasons of simplicity. In other words, among other things, FIG. 18 illustrates a spectral stimulation block in a time domain that is reserved for the spectral stimulation pulses, but the individual spectral stimulation pulses are not specifically illustrated in FIG. 18 for reasons of simplicity. In more detail, FIG. 18 illustrates the spectral stimulation block as a "gap"—an available time period in which the spread-spectrum pulses can occur. The "gap" is denoted as $t_{spectrum}$, and it can be calculated as a function of the following: a period of the tonic pulses (denoted as $t_{tonic}$), a pulse width of each tonic pulse (denoted as $PW_{tonic}$), a time length of the recovery phase of the tonic pulse PW (denoted as $t_{recov\_tonic}$), and a time length of the recovery phase of the spread-spectrum stimulation pulses (denoted as $t_{recov\_spec}$). In some embodiments, $t_{spectrum} = t_{tonic} - PW_{tonic} - t_{recov\_tonic} - t_{recov\_spec}$. Also, it is understood that even though FIG. 18 illustrates the recovery phases for the tonic stimulation and the spectral stimulation as being passive recovery phases, they may be active recovery phases in other embodiments, and the formula for calculating $t_{spectrum}$ remains the same.

It is understood that the spread spectrum pulses discussed above are different from burst pulses (also referred to as burst stimulation). Examples of burst pulses are described in U.S. Pat. No. 8,364,273 entitled "Combination of Tonic and Burst Stimulations to Treat Neurological Disorders". In burst stimulation, the waveform may include tonic pulses and burst pulses that have different frequencies from the tonic pulses. However, the burst pulses still have a fixed frequency, even if that fixed frequency is different from the fixed frequency of the tonic pulses. As such, the burst pulses have fixed periods in the time domain for any given waveform. In contrast, the spread spectrum pulses discussed above have no fixed frequency for a given duration of time (demonstrated by the lack of a single "peak" of the spread spectrum pulses in FIG. 14), and they do not have fixed periods (demonstrated by the uneven/unequal time periods 1010 and 1011 in FIG. 14, which is also shown as "jitter").

It is also understood that although the embodiments discussed above have demonstrated a stimulation waveform with a fixed frequency tonic component, the fixed frequency is not required for the tonic component either. For example, in some alternative embodiments, the tonic pulses may have multiple frequencies, for example the tonic pulses may have a first frequency of 60 Hz for a first period of time (e.g., 10 minutes), and then change into a second frequency of 50 Hz for a second period of time (e.g., another 10 minutes after the first 10 minutes). In such an embodiment, the tonic pulse component still has a fixed frequency for any given period of time while the spread-spectrum pulses continually shift in frequency, but that the tonic pulse component may still shift in frequency (e.g., for one low frequency to another low frequency) from time to time. In further embodiments, it is understood that the tonic pulse component may also have a spread-spectrum-like behavior. For example, even within a given period of time, the tonic pulse component (or rather, the low frequency component, since it no longer has a fixed frequency) may have varying frequencies, which may manifest in the time domain as not having fixed periods between adjacent pulses.

One benefit offered by the stimulation waveform discussed above (e.g., the stimulation waveform 1000) is that it prevents habituation. Habituation may refer to the neurons getting accustomed to the same stimulation frequency, and as such the neurons become less responsive to being stimulated by that same stimulation frequency. Consequently, this degrades the efficacy of the stimulation therapy. Another example of habituation may refer to an audio noise generated by the pulse generator, which can be detected by some patients as a high pitched buzz. This audio noise may become annoying to these patients. In comparison to most conventional neuro-stimulation systems that only generate pulses with a fixed frequency, the pulse generator of the present disclosure generates a stimulation waveform 1000 that includes the spread-spectrum component, which as discussed above does not have a fixed stimulation frequency. Thus, the stimulation waveform 1000 can effectively prevent or at least reduce the undesirable habituation.

As another benefit, the stimulation waveform 1000 offers better efficacy for patients compared to conventional stimulation waveforms. This is attributed to the fact that the stimulation waveform 1000 includes both the low frequency tonic component and the high frequency spread spectrum component. The tonic component can induce paresthesia, whose coverage area can be configured (e.g., by adjusting the stimulation parameters associated with the tonic stimulation) to mask pain. The spread spectrum component, which may be configured to be subthreshold (e.g., below a perception threshold or a paresthesia threshold), may provide additional therapeutic relief where paresthesia may be inadequate.

The foregoing has outlined features of several embodiments so that those skilled in the art may better understand the detailed description that follows. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A pulse generator, comprising:
communication circuitry configured to receive programming instructions sent from one or more electronic programming devices; and
stimulation circuitry configured to generate electrical pulses based on the received programming instructions, wherein:
when viewed in a frequency domain, the electrical pulses have a tonic component and a spread-spectrum component different from the tonic component;
the tonic component and the spread-spectrum component are simultaneously viewable in the frequency domain; and
the spread-spectrum component spans a substantially wider frequency range than the tonic component in the frequency domain, wherein the spread-spectrum component comprises a plurality of non-periodic electrical pulses when viewed in a time domain, and wherein an amount of time between each adjacent pair of the non-periodic electrical pulses is variable.

2. The pulse generator of claim 1, wherein when the electrical pulses are delivered to a patient:
the tonic component induces paresthesia; and
the spread-spectrum component does not induce paresthesia.

3. The pulse generator of claim 1, wherein:
the tonic component has a fixed frequency.

4. The pulse generator of claim 1, wherein: the spread-spectrum component corresponds to non-periodic electrical pulses when viewed in a time domain.

5. The pulse generator of claim 1, wherein the amount of time between each adjacent pair of the non-periodic electrical pulses is defined by a pseudo-random number generator located within the stimulation circuitry.

6. The pulse generator of claim 1, wherein:
the tonic component spans a first frequency range; and
the spread-spectrum component spans a second frequency range that is at least an order of magnitude larger than the first frequency range.

7. The pulse generator of claim 6, wherein:
the first frequency range has a center frequency f1 that is below one kilo-hertz (kHz);
the second frequency range is defined by a lower frequency limit f2 and a higher frequency limit f3; and
the lower frequency limit f2 and the higher frequency limit f3 are each in a kHz-range.

8. The pulse generator of claim 7, wherein the higher frequency limit f3 is several kHz larger than the lower frequency limit f2.

9. The pulse generator of claim 7, wherein the center frequency f1 is several tens of hertz.

10. The pulse generator of claim 7, wherein the center frequency f1 is several hundreds of hertz.

11. The pulse generator of claim 1, wherein a magnitude of the tonic component is substantially greater than a magnitude of the spread-spectrum component.

12. A method, comprising:
receiving, via communication circuitry on a pulse generator, programming instructions from a programming device that is external to the pulse generator; and
generating, based on the received programming instructions, electrical pulses via stimulation circuitry on the pulse generator, wherein:
the electrical pulses have a fixed-frequency component and a spread-spectrum component;
the fixed-frequency component and the spread-spectrum component are simultaneously viewable in a frequency domain;
the spread-spectrum component spans a substantially wider frequency range than the fixed-frequency component in the frequency domain;
the spread-spectrum component comprises a plurality of non-periodic electrical pulses viewable in a time domain; and
an amount of time between each adjacent pair of the non-periodic electrical pulses is pseudo-randomly generated.

13. The method of claim 12, further comprising: delivering the electrical pulses to a patient;
wherein:
the fixed-frequency component induces paresthesia when delivered to the patient; and
the spread-spectrum component does not induce paresthesia when delivered to the patient.

14. The method of claim 12, wherein the generating comprises:
generating a plurality of pseudo-random numbers via a pseudo-random number generator; and
defining the amount of time between each adjacent pair of the non-periodic electrical pulses at least in part using the plurality of pseudo-random numbers.

15. The method of claim 12, wherein a frequency range spanned by the spread-spectrum component is at least ten times wider than a frequency range spanned by the fixed-frequency component in the frequency domain.

16. The method of claim 12, wherein:
a frequency of the fixed-frequency component is several tens of hertz; and
a lower limit of the spread-spectrum component is several kilo-hertz.

17. The method of claim 12, wherein a magnitude of the fixed-frequency component is substantially greater than a magnitude of the spread-spectrum component.

18. A medical system, comprising:
an electronic programming device configured to generate programming instructions in response to user input; and
a pulse generator configured to generate electrical pulses based on the programming instructions;
wherein:
the electronic programming device or the pulse generator includes a pseudo-random number generator;
in a frequency spectrum, the electrical pulses simultaneously demonstrate at least a tonic component and a spread-spectrum component different from the tonic component;
the spread-spectrum component occupies a frequency range that is at least an order of magnitude wider than the tonic component in the frequency spectrum;
the spread-spectrum component comprises a plurality of pulses viewable in a time domain; and
an amount of time between each preceding pulse and a subsequent pulse of the plurality of pulses is defined by an output of the pseudo-random number generator.

19. The medical system of claim 18, wherein:
the tonic component is configured to induce paresthesia in a patient;
the spread-spectrum component is configured to not induce paresthesia in the patient; and
an amplitude of the tonic component is greater than an amplitude of the spread-spectrum component.

20. The medical system of claim 18, wherein in the time domain:
- the tonic component corresponds to a plurality of first pulses having a fixed period between adjacent first pulses; and
- the amount of time between each preceding pulse and the subsequent pulse of the plurality of pulses of the spread-spectrum component is different from the fixed period.

* * * * *